(12) United States Patent
Miyaji et al.

(10) Patent No.: US 7,851,503 B2
(45) Date of Patent: Dec. 14, 2010

(54) THROMBOPOETIN RECEPTOR ACTIVATOR AND PROCESS FOR PRODUCING THE SAME

(75) Inventors: Katsuaki Miyaji, Chiba (JP); Norihisa Ishiwata, Saitama (JP); Takanori Nakamura, Saitama (JP); Taito Nishino, Saitama (JP); Hisao Kamiya, Tokyo (JP); Masao Yamamoto, Saitama (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 1116 days.

(21) Appl. No.: 10/524,666

(22) PCT Filed: Aug. 14, 2003

(86) PCT No.: PCT/JP03/10353

§ 371 (c)(1),
(2), (4) Date: Feb. 11, 2005

(87) PCT Pub. No.: WO2004/016264

PCT Pub. Date: Feb. 26, 2004

(65) Prior Publication Data

US 2005/0282730 A1   Dec. 22, 2005

(30) Foreign Application Priority Data

Aug. 14, 2002 (JP) ............................. 2002-236167

(51) Int. Cl.
*A61K 31/275* (2006.01)
(52) U.S. Cl. .................................................. 514/525
(58) Field of Classification Search .................. 558/302; 514/525

See application file for complete search history.

(56) References Cited

U.S. PATENT DOCUMENTS 5,312,833 A * 5/1994 Tsuruoka et al. ............ 514/525

FOREIGN PATENT DOCUMENTS

| EP | 339671 | 11/1989 |
|---|---|---|
| JP | 02-040324 | 2/1990 |
| JP | 02-304058 | 12/1990 |
| JP | 04-182427 | 6/1992 |
| JP | 07-069883 | 3/1995 |
| JP | 07/107989 | 4/1995 |
| JP | 10-072492 | 3/1998 |
| JP | 11-001477 | 1/1999 |
| JP | 11-152276 | 6/1999 |
| JP | 2001-097948 | 4/2001 |
| WO | 94/20456 | 9/1994 |
| WO | 96/40189 | 12/1996 |
| WO | 96/40750 | 12/1996 |
| WO | 97/14704 | 4/1997 |
| WO | 98/25965 | 6/1998 |
| WO | 99/11262 | 3/1999 |
| WO | 00/35446 | 6/2000 |
| WO | 00/66112 | 11/2000 |
| WO | 01/07423 | 2/2001 |
| WO | 01/17349 | 3/2001 |
| WO | 01/21180 | 3/2001 |
| WO | 01/34585 | 5/2001 |
| WO | 01/39773 | 6/2001 |
| WO | 01/53267 | 7/2001 |
| WO | 01/89457 | 11/2001 |
| WO | 02/49413 | 6/2002 |
| WO | 02/059099 | 8/2002 |
| WO | 02/059100 | 8/2002 |
| WO | 02/062775 | 8/2002 |
| WO | 02/085343 | 10/2002 |

OTHER PUBLICATIONS

K. Pavithran, Thrombopoietin, Medicine On-Line.*
Saroj Vadhan-Raj et al., Stimulation of Megakaryocyte and Platelet Production by Single Dose of Recombinant Human Thrombopoietin in patients With Cancer,. Annals of Internal Medicine; vol. 126, Issue 9; May 1, 1997; pp. 673-681.*

(Continued)

*Primary Examiner*—James O. Wilson
*Assistant Examiner*—Ebenezer Sackey
(74) *Attorney, Agent, or Firm*—Oblon, Spivak, McClelland, Maier & Neustadt, L.L.P.

(57) ABSTRACT

A preventive, therapeutic or improving agent for diseases against which activation of the thrombopoietin receptor is effective or a platelet increasing agent, which contains a thrombopoietin receptor activator represented by the formula (1):

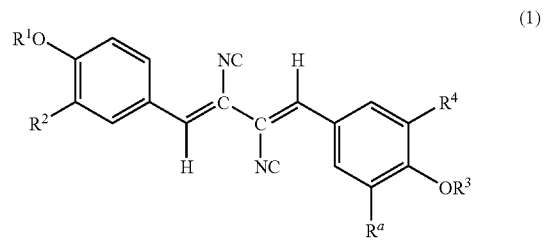

(1)

[wherein each of $R^1$ and $R^3$ is independently a hydrogen atom, $SO_3H$, a $C_{1-6}$ alkyl group, a $C_{1-6}$ alkylcarbonyl group or a $C_{6-18}$ arylcarbonyl group (the $C_{1-6}$ alkyl group, the $C_{1-6}$ alkylcarbonyl group and the $C_{6-18}$ arylcarbonyl group may be optionally substituted with a halogen atom, a hydroxyl group, a $C_{2-6}$ alkenyl group, a $C_{1-6}$ alkoxy group, a $C_{1-6}$ alkoxycarbonyl group, a $C_{6-18}$ aryl group, a 2-pyridyl group, a 3-pyridyl group, a 4-pyridyl group, a 2-furanyl group, a 3-furanyl group, a 2-thienyl group, a 3-thienyl group or $NR^9R^{10}$), and each of $R^2$, $R^4$ and $R^a$ is independently a hydrogen atom, a hydroxyl group or a $C_{1-6}$ alkoxy group].

17 Claims, 2 Drawing Sheets

OTHER PUBLICATIONS

Morino, T., "NK372135s, novel antifungal agents produced by *Neosartoria fischeri*.", J.Antibiot., vol. 47, No. 12, pp. 1546-1548, 1994.
Andrews, S., "Further Studies on the Water Relations of Xerophilic Fungi Including Some Halophiles.", J.Gen.Microbiol., vol. 133, No. 2, pp. 233-238, 1987.
U.S. Appl. No. 11/721,786, filed Jun. 14, 2007, Miyaji, et al.
U.S. Appl. No. 11/721,252, filed Jun, 8, 2007, Miyaji, et al.
Cardier, Jose E. "Effects of Megakaryocyte Growth and Development Factor (Thrombopoietin) on Liver Endothelial Cells in Vitro", Microvascular Research, vol. 58, pp. 108-113 1999.
Brizzi, Maria et al. "Thrombopoietin Stimulates Endothelial Cell Motility and Neoangiogenesis by a Platelet-Activating Factor-Dependent Mechanism", Circ Res., vol. 84, pp. 785-796 1999.
"Blood", Journal of the American Society of Hematology, vol. 98, No. 11, pp. 71a-72a 2001.
Morino, Tomio et al. "NK372135s, Novel Antifungal Agents Produced by *Neosartoila fischeri*", Journal of Antibiotics, vol. 47, No. 12, pp. 1546-1548 1994.
Andrews, S. et al. "Further Studies on the Water Relations of Xerophilic Fungi, Including Some Halophiles", Journal of General Microbiology, vol. 133, pp. 233-238 1987.
U.S. Appl. No. 12/492,435, filed Jun. 26, 2009, Owada, et al.

* cited by examiner

THROMBOPOETIN RECEPTOR ACTIVATOR AND PROCESS FOR PRODUCING THE SAME

TECHNICAL FIELD

The present invention relates to preventive, therapeutic and improving agents having affinity for and agonistic action on the thrombopoietin receptor for diseases against which activation of the thrombopoietin receptor is effective. Specifically, it relates to pharmaceutical compositions comprising compounds which increase platelets through stimulation of differentiation and proliferation of hematopoietic stem cells, megakaryocytic progenitor cells and megakaryocytes or compounds used for therapeutic angiogenesis or with anti-arteriosclerosis action that stimulate differentiation and proliferation of vascular endothelial cells and endothelial progenitor cells.

BACKGROUND ART

Thrombopoietin is a cytokine consisting of 332 amino acids that increases platelet production by stimulating differentiation and proliferation of hematopoietic stem cells, megakaryocytic progenitor cells and megakaryocytes mediated by its receptor and therefore is promising as a drug for hematological disorders. Recent reports that it stimulates differentiation and proliferation of vascular endothelial cells and endothelial progenitor cells have raised expectations of therapeutic angiogenesis, anti-arteriosclerosis and prevention of cardiovascular events (Microvasc. Res., 1999:58, 108-113, Circ. Res., 1999:84, 785-796, Blood 2001:98, 71a). Biologically active substances which have been known so far to regulate platelet production through the thrombopoietin receptor include, in addition to thrombopoietin itself, the low molecular weight peptides having affinity for the thrombopoietin receptor disclosed in JP-A-10-72492 (WO96/40750), WO96/40189, WO98/25965 and the like. As a result of search for nonpeptidic low molecular weight compounds that increase platelet production mediated by the thrombopoietin receptor, several reports have been made on low molecular weight compounds having affinity for the thrombopoietin receptor.

1) Applications filed by Hokuriku Seiyaku Co., Ltd. relating to 1,4-benzodiazepine derivatives (JP-A-11-1477 and JP-A-11-152276)
2) International Laid-open Patent Applications filed by Shionogi & Co., Ltd. (WO01/07423, WO01/53267, WO02/059099 and WO02/059100)
3) International Laid-open Patent Applications filed by SmithKline Beecham Corp (WO00/35446, WO00/66112, WO01/34585, WO01/17349, WO01/39773, WO01/21180, WO01/89457, WO02/49413 and WO02/085343)
4) Japanese Laid-open Patent Application filed by Torii Pharmaceutical Co., Ltd. (JP-A-2001-97948)
5) International Laid-open Patent Application filed by Roche Diagnostics GMBH (WO99/11262)
6) International Laid-open Patent Application filed by Yamanouchi Pharmaceutical Co., Ltd. (WO02/06275)

Meanwhile, xanthocillin analogues are not only known to have broad antibacterial spectra but also reported to have antiviral action, aromatase inhibitory action (JP-A-07-69883), antitumor medicine (JP-A-02-304058 and JP-A-04-182427), anthelmintic agent (JP-A-02-40324), prostaglandin synthesis inhibitory action and platelet aggregation inhibitory action. However, nothing has been reported on affinity for or agonistic action on the thrombopoietin receptor.

Thrombopoietin and low molecular weight peptides having affinity for the thrombopoietin receptor are likely to be easily degraded in the gastrointestinal tract and are usually difficult to orally administer. As to thrombopoietin itself, the appearance of anti-thrombopoietin antibodies have been reported.

Besides, though it is probably possible to orally administer nonpeptidic low molecular weight compounds, no practical drugs have been put on the market.

Therefore, orally administrable low molecular weight compounds having excellent affinity for and agonistic action on the thrombopoietin receptor as preventive, therapeutic and improving agents for diseases against which activation of the thrombopoietin receptor is effective have been demanded. Specifically, low molecular weight compounds which can serve as platelet increasing agents or increasing agents for other blood cells by stimulating differentiation and proliferation of hematopoietic stem cells, megakaryocytic progenitor cells and megakaryocytes or low molecular weight compounds which can be used for therapeutic angiogenesis or as preventive and therapeutic agents for arteriosclerosis by stimulating endothelial cells and endothelial progenitor cells have been demanded.

DISCLOSURE OF THE INVENTION

The present inventors conducted extensive research to find low molecular weight compounds having affinity for and agonistic action on the thrombopoietin receptor, and as a result, unexpectedly found that conventionally known xanthocillin and its analogues and their derivatives have high affinity for and agonistic action on the thrombopoietin receptor and found a novel process for producing xanthocillin analogues. The present invention was accomplished on the basis of this discovery.

Namely, the present invention relates to a thrombopoietin receptor activator represented by the formula (1)

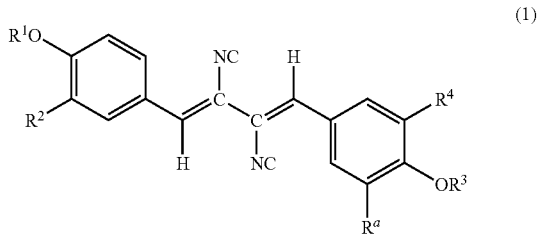

[wherein each of $R^1$ and $R^3$ is independently a hydrogen atom, $SO_3H$, a $C_{1-6}$ alkyl group, a $C_{1-6}$ alkylcarbonyl group or a $C_{6-18}$ arylcarbonyl group (the $C_{1-6}$ alkyl group, the $C_{1-6}$ alkylcarbonyl group and the $C_{6-18}$ arylcarbonyl group may be optionally substituted with a halogen atom, a hydroxyl group, a $C_{2-6}$ alkenyl group, a $C_{1-6}$ alkoxy group, a $C_{1-6}$ alkoxycarbonyl group, a $C_{6-18}$ aryl group, a 2-pyridyl group, a 3-pyridyl group, a 4-pyridyl group, a 2-furanyl group, a 3-furanyl group, a 2-thienyl group, a 3-thienyl group (the $C_{6-18}$ aryl group, the 2-pyridyl group, the 3-pyridyl group, the 4-pyridyl group, the 2-furanyl group, the 3-furanyl group, the 2-thienyl group and the 3-thienyl group may be optionally substituted with a halogen atom or a $C_{1-6}$ alkyl group) or $NR^9R^{10}$ (wherein each of $R^9$ and $R^{10}$ is independently a hydrogen atom or a $C_{1-6}$ alkyl group (the $C_{1-6}$ alkyl group may be optionally substituted with a $C_{6-18}$ aryl group) or $R^9$ and $R^{10}$ mean, together with each other, $-(CH_2)_nX(CH_2)_m-$ (wherein X is $CR^{11}R^{12}$ (wherein each of $R^{11}$ and $R^{12}$ is independently a hydrogen atom or a $C_{1-6}$ alkyl group (the $C_{1-6}$ alkyl group may be optionally substituted with a $C_{6-18}$ aryl group)), $NR^{13}$ (wherein $R^{13}$ is a hydrogen atom or a $C_{1-6}$ alkyl group (the $C_{1-6}$ alkyl group may be optionally substituted with a $C_{6-18}$ aryl group)), O or S, n is 1, 2 or 3, and m is 1, 2 or 3, provided that n+m is 3, 4 or 5))), and each of $R^2$, $R^4$ and $R^a$ is independently a hydrogen atom, a hydroxyl group or a $C_{1-6}$ alkoxy group], a preventive, therapeutic or improving agent against which activation of the thrombopoietin receptor is effective, which contains the thrombopoietin receptor activator or a prodrug, pharmaceutically acceptable salt or solvate thereof, as an active ingredient, a platelet increasing agent containing the thrombopoietin receptor activator or a prodrug, pharmaceutically acceptable salt or solvate thereof, as an active ingredient, a process for producing a compound represented by the formula (2), which comprises incubating a microorganism belonging to the *Basipetospora* genus and isolating the compound from the culture medium

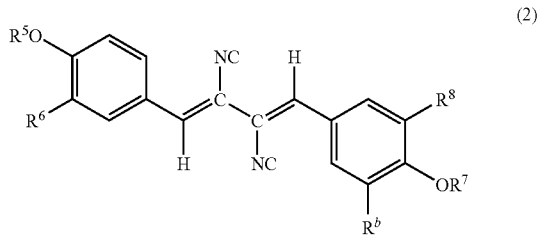

(2)

(wherein each of $R^5$ and $R^7$ is independently a hydrogen atom or a methyl group, and each of $R^6$, $R^8$ and $R^b$ is independently a hydrogen atom, a hydroxyl group or a methoxy group), *Basipetospora* sp. strain No. 1142 which is deposited under accession number FERM P-18940 and a compound represented by the formula (3).

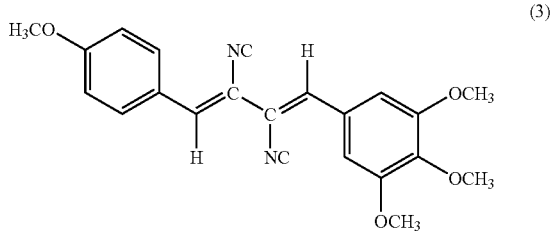

(3)

BEST MODE FOR CARRYING OUT THE INVENTION

Figure 1:
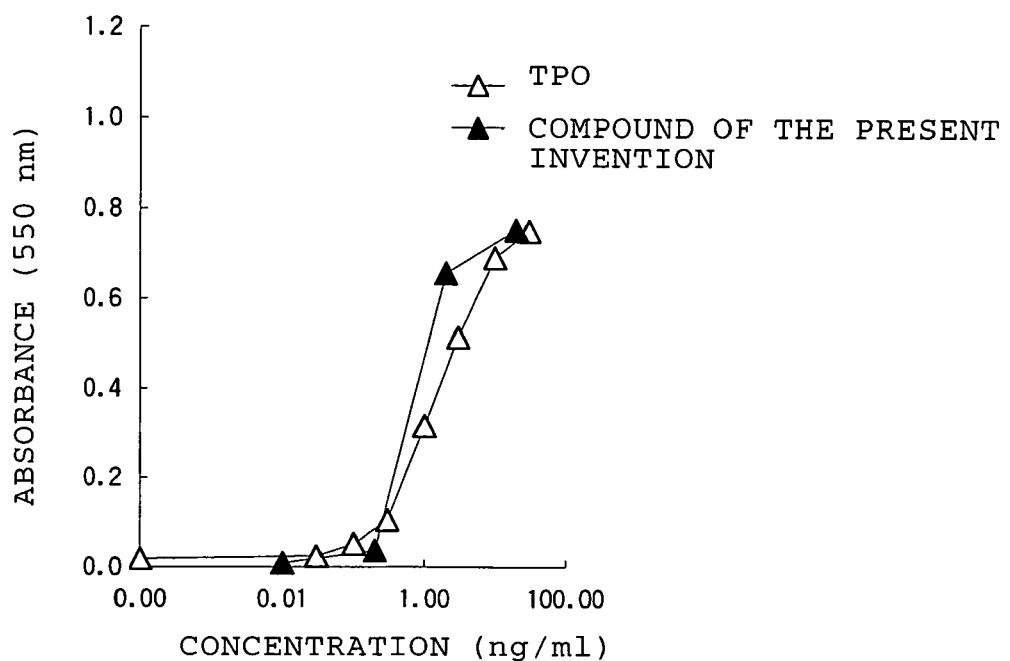
FIG. 1: Evaluation of the effect of the compound of the present invention (xanthocillin X monomethyl ether) on the proliferation of UT7/EPO-mpl cells by the MTT assay.

Now, the present invention will be described in detail.
In the present invention, "n" denotes normal, "i" denotes iso, "s" denotes secondary, "t" denotes tertiary, "c" denotes cyclo, "o" denotes ortho, "m" denotes meta, and "p" denotes para.

First, the terms in the respective substituents $R^1$, $R^2$, $R^3$, $R^4$ and $R^a$ will be explained.

A $C_{1-6}$ alkyl group may be linear, branched or cyclic (a $C_{3-6}$ cycloalkyl group), and methyl, ethyl, n-propyl, i-propyl, c-propyl, n-butyl, i-butyl, s-butyl, t-butyl, c-butyl, 1-methyl-c-propyl, 2-methyl-c-propyl, n-pentyl, 1-methyl-n-butyl, 2-methyl-n-butyl, 3-methyl-n-butyl, 1,1-dimethyl-n-propyl, 1,2-dimethyl-n-propyl, 2,2-dimethyl-n-propyl, 1-ethyl-n-propyl, c-pentyl, 1-methyl-c-butyl, 2-methyl-c-butyl, 3-methyl-c-butyl, 1,2-dimethyl-c-propyl, 2,3-dimethyl-c-propyl, 1-ethyl-c-propyl, 2-ethyl-c-propyl, n-hexyl, 1-methyl-n-pentyl, 2-methyl-n-pentyl, 3-methyl-n-pentyl, 4-methyl-n-pentyl, 1,1-dimethyl-n-butyl, 1,2-dimethyl-n-butyl, 1,3-dimethyl-n-butyl, 2,2-dimethyl-n-butyl, 2,3-dimethyl-n-butyl, 3,3-dimethyl-n-butyl, 1-ethyl-n-butyl, 2-ethyl-n-butyl, 1,1,2-trimethyl-n-propyl, 1,2,2-trimethyl-n-propyl, 1-ethyl-1-methyl-n-propyl, 1-ethyl-2-methyl-n-propyl, c-hexyl, 1-methyl-c-pentyl, 2-methyl-c-pentyl, 3-methyl-c-pentyl, 1-ethyl-c-butyl, 2-ethyl-c-butyl, 3-ethyl-c-butyl, 1,2-dimethyl-c-butyl, 1,3-dimethyl-c-butyl, 2,2-dimethyl-c-butyl, 2,3-dimethyl-c-butyl, 2,4-dimethyl-c-butyl, 3,3-dimethyl-c-butyl, 1-n-propyl-c-propyl, 2-n-propyl-c-propyl, 1-i-propyl-c-propyl, 2-i-propyl-c-propyl, 1,2,2-trimethyl-c-propyl, 1,2,3-trimethyl-c-propyl, 2,2,3-trimethyl-c-propyl, 1-ethyl-2-methyl-c-propyl, 2-ethyl-1-methyl-c-propyl, 2-ethyl-2-methyl-c-propyl, 2-ethyl-3-methyl-c-propyl and the like may be mentioned.

A $C_{1-6}$ alkylcarbonyl group may be linear, branched or cyclic (a $C_{3-6}$ cycloalkylcarbonyl group), and methylcarbonyl, ethylcarbonyl, n-propylcarbonyl, i-propylcarbonyl, c-propylcarbonyl, n-butylcarbonyl, i-butylcarbonyl, s-butylcarbonyl, t-butylcarbonyl, c-butylcarbonyl, 1-methyl-c-propylcarbonyl, 2-methyl-c-propylcarbonyl, n-pentylcarbonyl, 1-methyl-n-butylcarbonyl, 2-methyl-n-butylcarbonyl, 3-methyl-n-butylcarbonyl, 1,1-dimethyl-n-propylcarbonyl, 1,2-dimethyl-n-propylcarbonyl, 2,2-dimethyl-n-propylcarbonyl, 1-ethyl-n-propylcarbonyl, c-pentylcarbonyl, 1-methyl-c-butylcarbonyl, 2-methyl-c-butylcarbonyl, 3-methyl-c-butylcarbonyl, 1,2-dimethyl-c-propylcarbonyl, 2,3-dimethyl-c-propylcarbonyl, 1-ethyl-c-propylcarbonyl, 2-ethyl-c-propylcarbonyl, n-hexylcarbonyl, 1-methyl-n-pentylcarbonyl, 2-methyl-n-pentylcarbonyl, 3-methyl-n-pentylcarbonyl, 4-methyl-n-pentylcarbonyl, 1,1-dimethyl-n-butylcarbonyl, 1,2-dimethyl-n-butylcarbonyl, 1,3-dimethyl-n-butylcarbonyl, 2,2-dimethyl-n-butylcarbonyl, 2,3-dimethyl-n-butylcarbonyl, 3,3-dimethyl-n-butylcarbonyl, 1-ethyl-n-butylcarbonyl, 2-ethyl-n-butylcarbonyl, 1,1,2-trimethyl-n-propylcarbonyl, 1,2,2-trimethyl-n-propylcarbonyl, 1-ethyl-1-methyl-n-propylcarbonyl, 1-ethyl-2-methyl-n-propylcarbonyl, c-hexylcarbonyl, 1-methyl-c-pentylcarbonyl, 2-methyl-c-pentylcarbonyl, 3-methyl-c-pentylcarbonyl, 1-ethyl-c-butylcarbonyl, 2-ethyl-c-butylcarbonyl, 3-ethyl-c-butylcarbonyl, 1,2-dimethyl-c-butylcarbonyl, 1,3-dimethyl-c-butylcarbonyl, 2,2-dimethyl-c-butylcarbonyl, 2,3-dimethyl-c-butylcarbonyl, 2,4-dimethyl-c-butylcarbonyl, 3,3-dimethyl-c-butylcarbonyl, 1-n-propyl-c-propylcarbonyl, 2-n-propyl-c-propylcarbonyl, 1-i-propyl-c-propycarbonyl, 2-i-propyl-c-propylcarbonyl, 1,2,2-trimethyl-c-propylcarbonyl, 1,2,3-trimethyl-c-propylcarbonyl, 2,2,3-trimethyl-c-propylcarbonyl, 1-ethyl-2-methyl-c-propylcarbonyl, 2-ethyl-1-methyl-c-propylcarbonyl, 2-ethyl-2-methyl-c-propylcarbonyl, 2-ethyl-3-methyl-c-propylcarbonyl or the like may be mentioned.

As a $C_{6-18}$ arylcarbonyl group, a benzoyl group, a 1-indenylcarbonyl group, a 2-indenylcarbonyl group, a 3-indenylcarbonyl group, a 4-indenylcarbonyl group, a 5-indenylcarbonyl group, a 6-indenylcarbonyl group, a 7-indenylcarbonyl group, an α-naphthylcarbonyl group, a β-naphthylcarbonyl group, a 1-tetrahydronaphthylcarbonyl group, a 2-tetrahydronaphthylcarbonyl group, a 5-tetrahydronaphthylcarbonyl group, a 6-tetrahydronaphthylcarbonyl group, an o-biphenylylcarbonyl group, a m-biphenylylcarbonyl group, a p-biphenylylcarbonyl group, a 1-anthrylcarbonyl group, a 2-anthrylcarbonyl group, a 9-anthrylcarbonyl group, a 1-phenanthrylcarbonyl group, a 2-phenanthrylcarbonyl group, a 3-phenanthrylcarbonyl group, a 4-phenanthrylcarbonyl group, a 9-phenanthrylcarbonyl group or the like may be mentioned.

As a $C_{6-18}$ aryl group, a phenyl group, a 1-indenyl group, a 2-indenyl group, a 3-indenyl group, a 4-indenyl group, a 5-indenyl group, a 6-indenyl group, a 7-indenyl group, an α-naphthyl group, a β-naphthyl group, a 1-tetrahydronaphthyl group, a 2-tetrahydronaphthyl group, a 5-tetrahydronaphthyl group, a 6-tetrahydronaphthyl group, an o-biphenylyl group, a m-biphenylyl group, a p-biphenylyl group, a 1-anthryl group, a 2-anthryl group, a 9-anthryl group, a 1-phenanthryl group, a 2-phenanthryl group, a 3-phenanthryl group, a 4-phenanthryl group, a 9-phenanthryl group or the like may be mentioned.

As a halogen atom, a fluorine atom, a chlorine atom, a bromine atom or an iodine atom may be mentioned.

A $C_{2-6}$ alkenyl group may be linear, branched or cyclic (a $C_{3-6}$ cycloalkenyl group), and ethenyl, 1-propenyl, 2-propenyl, 1-methyl-1-ethenyl, 1-butenyl, 2-butenyl, 3-butenyl, 2-methyl-1-propenyl, 2-methyl-2-propenyl, 1-ethylethenyl, 1-methyl-1-propenyl, 1-methyl-2-propenyl, 1-pentenyl, 2-pentenyl, 3-pentenyl, 4-pentenyl, 1-n-propylethenyl, 1-methyl-1-butenyl, 1-methyl-2-butenyl, 1-methyl-3-butenyl, 2-ethyl-2-propenyl, 2-methyl-1-butenyl, 2-methyl-2-butenyl, 2-methyl-3-butenyl, 3-methyl-1-butenyl, 3-methyl-2-butenyl, 3-methyl-3-butenyl, 1,1-dimethyl-2-propenyl, 1-i-propylethenyl, 1,2-dimethyl-1-propenyl, 1,2-dimethyl-2-propenyl, 1-c-pentenyl, 2-c-pentenyl, 3-c-pentenyl, 1-hexenyl, 2-hexenyl, 3-hexenyl, 4-hexenyl, 5-hexenyl, 1-methyl-1-pentenyl, 1-methyl-2-pentenyl, 1-methyl-3-pentenyl, 1-methyl-4-pentenyl, 1-n-butylethenyl, 2-methyl-1-pentenyl, 2-methyl-2-pentenyl, 2-methyl-3-pentenyl, 2-methyl-4-pentenyl, 2-n-propyl-2-propenyl, 3-methyl-1-pentenyl, 3-methyl-2-pentenyl, 3-methyl-3-pentenyl, 3-methyl-4-pentenyl, 3-ethyl-3-butenyl, 4-methyl-1-pentenyl, 4-methyl-2-pentenyl, 4-methyl-3-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1-methyl-2-ethyl-2-propenyl, 1-s-butylethenyl, 1,3-dimethyl-1-butenyl, 1,3-dimethyl-2-butenyl, 1,3-dimethyl-3-butenyl, 1-i-butylethenyl, 2,2-dimethyl-3-butenyl, 2,3-dimethyl-1-butenyl, 2,3-dimethyl-2-butenyl, 2,3-dimethyl-3-butenyl, 2-i-propyl-2-propenyl, 3,3-dimethyl-1-butenyl, 1-ethyl-1-butenyl, 1-ethyl-2-butenyl, 1-ethyl-3-butenyl, 1-n-propyl-1-propenyl, 1-n-propyl-2-propenyl, 2-ethyl-1-butenyl, 2-ethyl-2-butenyl, 2-ethyl-3-butenyl, 1,1,2-trimethyl-2-propenyl, 1-t-butylethenyl, 1-methyl-1-ethyl-2-propenyl, 1-ethyl-2-methyl-1-propenyl, 1-ethyl-2-methyl-2-propenyl, 1-i-propyl-1-propenyl, 1-i-propyl-2-propenyl, 1-methyl-2-c-pentenyl, 1-methyl-3-c-pentenyl, 2-methyl-1-c-pentenyl, 2-methyl-2-c-pentenyl, 2-methyl-3-c-pentenyl, 2-methyl-4-c-pentenyl, 2-methyl-5-c-pentenyl, 2-methylene-c-pentyl, 3-methyl-1-c-pentenyl, 3-methyl-2-c-pentenyl, 3-methyl-3-c-pentenyl, 3-methyl-4-c-pentenyl, 3-methyl-5-c-pentenyl, 3-methylene-c-pentyl, 1-c-hexenyl, 2-c-hexenyl, 3-c-hexenyl or the like may be mentioned.

A $C_{1-6}$ alkoxy group may be linear, branched or cyclic (a $C_{3-6}$ cycloalkoxy group), and methoxy, ethoxy, n-propoxy, i-propoxy, c-propoxy, n-butoxy, i-butoxy, s-butoxy, t-butoxy, c-butoxy, 1-methyl-c-propoxy, 2-methyl-c-propoxy, n-pentyloxy, 1-methyl-n-butoxy, 2-methyl-n-butoxy, 3-methyl-n-butoxy, 1,1-dimethyl-n-propoxy, 1,2-dimethyl-n-propoxy, 2,2-dimethyl-n-propoxy, 1-ethyl-n-propoxy, c-pentyloxy, 1-methyl-c-butoxy, 2-methyl-c-butoxy, 3-methyl-c-butoxy, 1,2-dimethyl-c-propoxy, 2,3-dimethyl-c-propoxy, 1-ethyl-c-propoxy, 2-ethyl-c-propoxy, n-hexyloxy, 1-methyl-n-pentyloxy, 2-methyl-n-pentyloxy, 3-methyl-n-pentyloxy, 4-methyl-n-pentyloxy, 1,1-dimethyl-n-butoxy, 1,2-dimethyl-n-butoxy, 1,3-dimethyl-n-butoxy, 2,2-dimethyl-n-butoxy, 2,3-dimethyl-n-butoxy, 3,3-dimethyl-n-butoxy, 1-ethyl-n-butoxy, 2-ethyl-n-butoxy, 1,1,2-trimethyl-n-propoxy, 1,2,2-trimethyl-n-propoxy, 1-ethyl-1-methyl-n-propoxy, 1-ethyl-2-methyl-n-propoxy, c-hexyloxy, 1-methyl-c-pentyloxy, 2-methyl-c-pentyloxy, 3-methyl-c-pentyloxy, 1-ethyl-c-butoxy, 2-ethyl-c-butoxy, 3-ethyl-c-butoxy, 1,2-dimethyl-c-butoxy, 1,3-dimethyl-c-butoxy, 2,2-dimethyl-c-butoxy, 2,3-dimethyl-c-butoxy, 2,4-dimethyl-c-butoxy, 3,3-dimethyl-c-butoxy, 1-n-propyl-c-propoxy, 2-n-propyl-c-propoxy, 1-i-propyl-c-propoxy, 2-i-propyl-c-propoxy, 1,2,2-trimethyl-c-propoxy, 1,2,3-trimethyl-c-propoxy, 2,2,3-trimethyl-c-propoxy, 1-ethyl-2-methyl-c-propoxy, 2-ethyl-1-methyl-c-propoxy, 2-ethyl-2-methyl-c-propoxy, 2-ethyl-3-methyl-c-propoxy or the like may be mentioned.

A $C_{1-6}$ alkoxycarbonyl group may be linear, branched or cyclic (a $C_{3-6}$ cycloalkoxycarbonyl group), and methoxycarbonyl, ethoxycarbonyl, n-propoxycarbonyl, i-propoxycarbonyl, c-propylcarbonyl, n-butoxycarbonyl, i-butoxycarbonyl, s-butoxycarbonyl, t-butoxycarbonyl, c-butoxycarbonyl, 1-methyl-c-propoxycarbonyl, 2-methyl-c-propoxycarbonyl, n-pentyloxycarbonyl, 1-methyl-n-butoxycarbonyl, 2-methyl-n-butoxycarbonyl, 3-methyl-n-butoxycarbonyl, 1,1-dimethyl-n-propoxycarbonyl, 1,2-dimethyl-n-propoxycarbonyl, 2,2-dimethyl-n-propoxycarbonyl, 1-ethyl-n-propoxycarbonyl, c-pentyloxycarbonyl, 1-methyl-c-butoxycarbonyl, 2-methyl-c-butoxycarbonyl, 3-methyl-c-butoxycarbonyl, 1,2-dimethyl-c-propoxycarbonyl, 2,3-dimethyl-c-propoxycarbonyl, 1-ethyl-c-propoxycarbonyl, 2-ethyl-c-propoxycarbonyl, n-hexyloxycarbonyl, 1-methyl-n-pentyloxycarbonyl, 2-methyl-n-pentyloxycarbonyl, 3-methyl-n-pentyloxycarbonyl, 4-methyl-n-pentyloxycarbonyl, 1,1-dimethyl-n-butoxycarbonyl, 1,2-dimethyl-n-butoxycarbonyl, 1,3-dimethyl-n-butoxycarbonyl, 2,2-dimethyl-n-butoxycarbonyl, 2,3-dimethyl-n-butoxycarbonyl, 3,3-dimethyl-n-butoxycarbonyl, 1-ethyl-n-butoxycarbonyl, 2-ethyl-n-butoxycarbonyl, 1,1,2-trimethyl-n-propoxycarbonyl, 1,2,2-trimethyl-n-propoxycarbonyl, 1-ethyl-1-methyl-n-propoxycarbonyl, 1-ethyl-2-methyl-n-propoxycarbonyl, c-hexyloxycarbonyl, 1-methyl-c-pentyloxycarbonyl, 2-methyl-c-pentyloxycarbonyl, 3-methyl-c-pentyloxycarbonyl, 1-ethyl-c-butoxycarbonyl, 2-ethyl-c-butoxycarbonyl, 3-ethyl-c-butoxycarbonyl, 1,2-dimethyl-c-butoxycarbonyl, 1,3-dimethyl-c-butoxycarbonyl, 2,2-dimethyl-c-butoxycarbonyl, 2,3-dimethyl-c-butoxycarbonyl, 2,4-dimethyl-c-butoxycarbonyl, 3,3-dimethyl-c-butoxycarbonyl, 1-n-propyl-c-propoxycarbonyl, 2-n-propyl-c-propoxycarbonyl, 1-i- propyl-c-propoxycarbonyl, 2-i-propyl-c-propoxycarbonyl, 1,2,2-trimethyl-c-propoxycarbonyl, 1,2,3-trimethyl-c-propoxycarbonyl, 2,2,3-trimethyl-c-propoxycarbonyl, 1-ethyl-2-methyl-c-propoxycarbonyl, 2-ethyl-1-methyl-c-propoxycarbonyl, 2-ethyl-2-methyl-c-propoxycarbonyl, 2-ethyl-3-methyl-c-propoxycarbonyl or the like may be mentioned.

Specific preferred examples of the substituents $R^1$ and $R^3$ which are independent of each other are a hydrogen atom, a methyl group, a n-hexyl group, a 2-fluoroethyl group, a benzyl group, a p-chlorophenyl group, a p-methylphenyl group, an ethoxycarbonylmethyl group, a 2-propenyl group, a 4-pyridylmethyl group, a 2-pyridylmethyl group, a methylcarbonyl group, a benzoyl group, a 2-ethylaminoethyl group, 2-(1-piperidino)-ethyl group and the like.

Specific preferred examples of the substituents $R^2$, $R^4$ and $R^a$ which are independent of one another are a hydrogen atom, a hydroxyl group and a methoxy group.

Favorable compounds as the thrombopoietin receptor activator represented by the formula (1), the compound to be used in the preventive, therapeutic or improving agent for diseases against which activation of the thrombopoietin receptor is effective and the compound to be used in the platelet increasing agent of the present invention are as follows.

1) Compounds represented by the formula (1) wherein each of each of $R^1$ and $R^3$ is independently a hydrogen atom, $SO_3H$, a $C_{1-6}$ alkyl group, a $C_{1-6}$ alkylcarbonyl group or a $C_{6-18}$ arylcarbonyl group (the $C_{1-6}$ alkyl group, the $C_{1-6}$ alkylcarbonyl group and the $C_{6-18}$ arylcarbonyl group may be optionally substituted with a hydroxyl group).

2) Compounds represented by the formula (1) wherein each of $R^1$ and $R^3$ is independently a hydrogen atom, $SO_3H$, a $C_{1-6}$ alkyl group, a $C_{1-6}$ alkylcarbonyl group or a $C_{6-18}$ arylcarbonyl group (the $C_{1-6}$ alkyl group, the $C_{1-6}$ alkylcarbonyl group and the $C_{6-18}$ arylcarbonyl group may be optionally substituted with $NR^9R^{10}$ (wherein each of $R^9$ and $R^{10}$ is independently a hydrogen atom or a $C_{1-6}$ alkyl group (the $C_{1-6}$ alkyl group may be optionally substituted with a $C_{6-18}$ aryl group) or $R^9$ and $R^{10}$ mean, together with each other, —$(CH_2)_n X(CH_2)_m$— (wherein X is $CR^{11}R^{12}$ (wherein each of $R^{11}$ and $R^{12}$ is independently a hydrogen atom or a $C_{1-6}$ alkyl group (the $C_{1-6}$ alkyl group may be optionally substituted with a $C_{6-18}$ aryl group)), $NR^{13}$ (wherein $R^{13}$ is a hydrogen atom or a $C_{1-6}$ alkyl group (the $C_{1-6}$ alkyl group may be optionally substituted with a $C_{6-18}$ aryl group)), O or S, n is 1, 2 or 3, and m is 1, 2 or 3, provided that n+m is 3, 4 or 5))).

3) Compounds represented by the formula (1) wherein each of $R^1$ and $R^3$ is independently a hydrogen atom or a $C_{1-6}$ alkyl group.

4) The compounds according to 3) wherein each of $R^1$ and $R^3$ is independently a hydrogen atom or a methyl group, and each of $R^2$ and $R^4$ is independently a hydrogen atom, a hydroxyl group or a methoxy group.

5) Compounds represented by the formula (1) or the compounds according to 1), 2), 3) or 4) wherein $R^2$ is a hydrogen atom.

6) Compounds according to 5) wherein each of $R^4$ and $R^a$ is independently a hydrogen atom or a methoxy group.

7) Compounds wherein $R^1$, $R^2$, $R^3$, $R^4$ and $R^a$ are any of the following combinations.
$R^1$=H, $R^2$=OH, $R^3$=H, $R^4$=OH, $R^a$=H
$R^1$=$CH_3$, $R^2$=$OCH_3$, $R^3$=$CH_3$, $R^4$=$OCH_3$, $R^a$=H
$R^1$=H, $R^2$=$OCH_3$, $R^3$=H, $R^4$=$OCH_3$, $R^a$=H
$R^1$=$CH_3$, $R^2$=OH, $R^3$=$CH_3$, $R^4$=OH, $R^a$=H
$R^1$=H, $R^2$=H, $R^3$=H, $R^4$=OH, $R^a$=H
$R^1$=$CH_3$, $R^2$=H, $R^3$=$CH_3$, $R^4$=$OCH_3$, $R^a$=H
$R^1$=$CH_3$, $R^2$=H, $R^3$=$CH_3$, $R^4$=OH, $R^a$=H
$R^1$=H, $R^2$=H, $R^3$=H, $R^4$=H, $R^a$=H
$R^1$=$CH_3$, $R^2$=H, $R^3$=$CH_3$, $R^4$=H, $R^1$=H
$R^1$=H, $R^2$=H, $R^3$=$CH_3$, $R^4$=H, $R^a$=H
$R^1$=$CH_3$, $R^2$=H, $R^3$=$SO_3H$, $R^4$=H, $R^a$=H
$R^1$=$CH_3$, $R^2$=H, $R^3$=$CH_3$, $R^4$=$OCH_3$, $R^a$=$OCH_3$ 8) Compounds wherein $R^1$, $R^2$, $R^3$, $R^4$ and $R^a$ are any of the following combinations.
$R^1$=H, $R^2$=H, $R^3$=H, $R^4$=H, $R^a$=H
$R^1$=$CH_3$, $R^2$=H, $R^3$=$CH_3$, $R^4$=H, $R^a$=H
$R^1$=H, $R^2$=H, $R^3$=$CH_3$, $R^4$=H, $R^a$=H
$R^1$=$CH_3$, $R^2$=H, $R^3$=$SO_3H$, $R^4$=H, $R^a$=H
$R^1$=$CH_3$, $R^2$=H, $R^3$=$CH_3$, $R^4$=$OCH_3$, $R^a$=H
$R^1$=$CH_3$, $R^2$=H, $R^3$=$CH_3$, $R^4$=$OCH_3$, $R^a$=$OCH_3$ 9) Compounds represented by the formula (1) wherein both $R^2$ and $R^4$ are both hydroxyl groups, or $R^2$ is a hydroxyl group and $R^4$ is hydrogen atom, and $R^1$ and $R^3$ are both hydrogen atoms.

10) Compounds represented by the formula (1) wherein $R^2$ are $R^4$ are both $C_{1-6}$ alkoxy groups, or $R^2$ is a $C_{1-6}$ alkoxy group and $R^4$ is hydrogen atom, and $R^1$ and $R^3$ are both $C_{1-6}$ alkyl groups.

11) Compounds represented by the formula (1) wherein $R^2$ and $R^4$ are both hydrogen atoms, and $R^1$ and $R^3$ are both hydrogen atoms, $SO_3H$, $C_{1-6}$ alkyl groups, $C_{1-6}$ alkylcarbonyl groups or $C_{6-18}$ arylcarbonyl groups (the $C_{1-6}$ alkyl groups, the $C_{1-6}$ alkylcarbonyl groups and the $C_{6-18}$ arylcarbonyl groups may be optionally substituted with a halogen atom, a hydroxyl group, a $C_{2-6}$ alkenyl group, a $C_{1-6}$ alkoxy group, a $C_{1-6}$ alkoxycarbonyl group, a $C_{6-18}$ aryl group, a 2-pyridyl group, a 3-pyridyl group, a 4-pyridyl group, a 2-furanyl group, a 3-furanyl group, a 2-thienyl group, a 3-thienyl group (the $C_{6-18}$ aryl group, the 2-pyridyl group, the 3-pyridyl group, the 4-pyridyl group, the 2-furanyl group, the 3-furanyl group, the 2-thienyl group and the 3-thienyl group may be optionally substituted with a halogen atom or a $C_{1-6}$ alkyl group) or $NR^9R^{10}$ (wherein each of $R^9$ and $R^{10}$ is independently a hydrogen atom or a $C_{1-6}$ alkyl group (the $C_{1-6}$ alkyl group may be optionally substituted with a $C_{6-18}$ aryl group) or $R^9$ and $R^{10}$ mean, together with each other, —$(CH_2)_n X(CH_2)_m$— (wherein X is $CR^{11}R^{12}$ (wherein each of $R^{11}$ and $R^{12}$ is independently a hydrogen atom or a $C_{1-6}$ alkyl group (the $C_{1-6}$ alkyl group may be optionally substituted with a $C_{6-18}$ aryl group)), $NR^{13}$ (wherein $R^{13}$ is a hydrogen atom or a $C_{1-6}$ alkyl group (the $C_{1-6}$ alkyl group may be optionally substituted with a $C_{6-18}$ aryl group)), O or S, n is 1, 2 or 3, and m is 1, 2 or 3, provided that n+m is 3, 4 or 5))).

12) Compounds represented by the formula (1) wherein $R^2$ and $R^4$ are both hydrogen atoms, $R^1$ is a methyl group, and $R^3$ is a hydrogen atom, $SO_3H$, a $C_{1-6}$ alkyl group, a $C_{1-6}$ alkylcarbonyl group or a $C_{6-18}$ arylcarbonyl group (the $C_{1-6}$ alkyl group, the $C_{1-6}$ alkylcarbonyl group and the $C_{6-18}$ arylcarbonyl group may be optionally substituted with a halogen atom, a hydroxyl group, a $C_{2-6}$ alkenyl group, a $C_{1-6}$ alkoxy group, a $C_{1-6}$ alkoxycarbonyl group, a $C_{6-18}$ aryl group, a 2-pyridyl group, a 3-pyridyl group, a 4-pyridyl group, a 2-furanyl group, a 3-furanyl group, a 2-thienyl group, a 3-thienyl group (the $C_{6-18}$ aryl group, the 2-pyridyl group, the 3-pyridyl group, the 4-pyridyl group, the 2-furanyl group, the 3-furanyl group, the 2-thienyl group and the 3-thienyl group may be optionally substituted with a halogen atom or a $C_{1-6}$ alkyl group) or $NR^9R^{10}$ (wherein each of $R^9$ and $R^{10}$ is independently a hydrogen atom or a $C_{1-6}$ alkyl group (the $C_{1-6}$ alkyl group may be optionally substituted with a $C_{6-18}$ aryl group) or $R^9$ and $R^{10}$ mean, together with each other, —$(CH_2)_n X (CH_2)_m$— (wherein X is $CR^{11}R^{12}$ (wherein each of $R^{11}$ and $R^{12}$ is independently a hydrogen atom or a $C_{1-6}$ alkyl group (the $C_{1-6}$ alkyl group may be optionally substituted with a $C_{6-18}$ aryl group)), $NR^{13}$ (wherein $R^{13}$ is a hydrogen atom or a C$_{1-6}$ alkyl group (the C$_{1-6}$ alkyl group may be optionally substituted with a C$_{6-18}$ aryl group)), O or S, n is 1, 2 or 3, and m is 1, 2 or 3, provided that n+m is 3, 4 or 5))).

Favorable compounds represented by the formula (2) are as follows.

13) Compounds wherein R$^5$, R$^6$, R$^7$, R$^8$ and R$^b$ are any of the following combinations.
R$^5$=H, R$^6$=OH, R$^7$=H, R$^8$=OH, R$^b$=H
R$^5$=CH$_3$, R$^6$=OCH$_3$, R$^7$=CH$_3$, R$^8$=OCH$_3$, R$^b$=H
R$^5$=H, R$^6$=OCH$_3$, R$^7$=H, R$^8$=OCH$_3$, R$^b$=H
R$^5$=CH$_3$, R$^6$=OH, R$^7$=CH$_3$, R$^8$=OH, R$^b$=H
R$^5$=H, R$^6$=H, R$^7$=H, R$^8$=OH, R$^b$=H
R$^5$=CH$_3$, R$^6$=H, R$^7$=CH$_3$, R$^8$=OCH$_3$, R$^b$=H
R$^5$=CH$_3$, R$^6$=H, R$^7$=CH$_3$, R$^8$=OH, R$^b$=H
R$^5$=H, R$^6$=H, R$^7$=H, R$^8$=H, R$^b$=H
R$^5$=CH$_3$, R$^6$=H, R$^7$=CH$_3$, R$^8$=H, R$^b$=H
R$^5$=H, R$^6$=H, R$^7$=CH$_3$, R$^8$=H, R$^b$=H
R$^5$=CH$_3$, R$^6$=H, R$^7$=CH$_3$, R$^8$=OCH$_3$, R$^b$=OCH$_3$ 14) Compounds wherein R$^5$, R$^6$, R$^7$, R$^8$ and R$^b$ are any of the following combinations.
R$^5$=H, R$^6$=H, R$^7$=H, R$^8$=H, R$^b$=H
R$^5$=CH$_3$, R$^6$=H, R$^7$=CH$_3$, R$^8$=H, R$^b$=H
R$^5$=H, R$^6$=H, R$^7$=CH$_3$, R$^8$=H, R$^b$=H
R$^5$=CH$_3$, R$^6$=H, R$^7$=CH$_3$, R$^8$=OCH$_3$, R$^b$=H
R$^5$=CH$_3$, R$^6$=H, R$^7$=CH$_3$, R$^8$=OCH$_3$, R$^b$=OCH$_3$ 15) Compounds wherein R$^5$, R$^6$, R$^7$, R$^8$ and R$^b$ are any of the following combinations.
R$^5$=CH$_3$, R$^6$=H, R$^7$=CH$_3$, R$^8$=H, R$^b$=H
R$^5$=H, R$^6$=H, R$^7$=CH$_3$, R$^8$=H, R$^b$=H
R$^5$=CH$_3$, R$^6$=H, R$^7$=CH$_3$, R$^8$=OCH$_3$, R$^b$=H
R$^5$=CH$_3$, R$^6$=H, R$^7$=CH$_3$, R$^8$=OCH$_3$, R$^b$=OCH$_3$ The compounds of the present invention represented by the formula (1) or pharmaceutically acceptable salts thereof may be in the form of arbitrary crystals or arbitrary hydrates, depending on the production conditions. The present invention covers these crystals, hydrates and mixtures. They may be in the form of solvates with organic solvents such as acetone, ethanol and tetrahydrofuran, and the present invention covers any of these forms.

The compounds of the present invention represented by the formula (1) may be converted to pharmaceutically acceptable salts or may be liberated from the resulting salts, if necessary. The pharmaceutically acceptable salts of the present invention may be, for example, salts with alkali metals (such as lithium, sodium and potassium), alkaline earth metals (such as magnesium and calcium), ammonium, organic bases and amino acids. They may be salts with inorganic acids (such as hydrochloric acid, hydrobromic acid, phosphoric acid and sulfuric acid) and organic acids (such as acetic acid, citric acid, maleic acid, fumaric acid, benzenesulfonic acid and p-toluenesulfonic acid).

The compounds which serve as prodrugs are derivatives of the present invention having chemically or metabolically degradable groups which give pharmacologically active compounds of the present invention upon solvolysis or under physiological conditions in vivo. Methods for selecting or producing appropriate prodrugs are disclosed, for example, in Design of Prodrug (Elsevier, Amsterdam 1985). In the present invention, when the compound has a hydroxyl group, acyloxy derivatives obtained by reacting the compound with appropriate acyl halides or appropriate acid anhydrides may, for example, be mentioned as prodrugs. Acyloxys particularly preferred as prodrugs include —OCOC$_2$H$_5$, —OCO(t-Bu), —OCOC$_{15}$H$_{31}$, —OCO(m-CO$_2$Na-Ph), —OCOCH$_2$CH$_2$CO$_2$Na, —OCOCH(NH$_2$)CH$_3$, —OCOCH$_2$N(CH$_3$)$_2$ and the like. When the compound of the present invention has an amino group, amide derivatives obtained by reacting the compound having an amino group with appropriate acid halides or appropriate mixed acid anhydrides may, for example, be mentioned as prodrugs. Amides particularly preferred as prodrugs include —NHCO(CH$_2$)$_{20}$OCH$_3$, —NHCOCH(NH$_2$)CH$_3$ and the like.

Medicines containing the thrombopoietin receptor activators of the present invention or prodrugs, pharmaceutically acceptable salts or solvates thereof as an active ingredient may usually be administered as oral medicines such as tablets, capsules, powder, granules, pills and syrup, as rectal medicines, percutaneous medicines or injections. The agents of the present invention may be administered as a single therapeutic agent or as a mixture with other therapeutic agents. Though they may be administered as they are, they are usually administered in the form of medical compositions. These pharmaceutical preparations can be obtained by adding pharmacologically and pharmaceutically acceptable additives by conventional methods. Namely, for oral medicines, ordinary excipients, lubricants, binders, disintegrants, humectants, plasticizers and coating agents may be used. Oral liquid preparations may be in the form of aqueous or oily suspensions, solutions, emulsions, syrups or elixirs or may be supplied as dry syrups to be mixed with water or other appropriate solvents before use. Such liquid preparations may contain ordinary additives such as suspending agents, perfumes, diluents and emulsifiers. In the case of rectal administration, they may be administered as suppositories. Suppositories may use an appropriate substance such as cacao butter, laurin tallow, Macrogol, glycerogelatin, Witepsol, sodium stearate and mixtures thereof as the base and may, if necessary, contain an emulsifier, a suspending agent, a preservative and the like. For injections, pharmaceutical ingredients such as distilled water for injection, physiological saline, 5% glucose solution, propylene glycol and other solvents or solubilizing agents, a pH regulator, an isotonizing agent and a stabilizer may be used to form aqueous dosage forms or dosage forms which need dissolution before use.

The dose of the agents of the present invention for administration to human is usually about from 0.1 to 1000 mg/human/day in the case of oral medicines or rectal administration and about from 0.05 mg to 500 mg/human/day in the case of injections, though it depends on the age and conditions of the patient. The above-mentioned ranges are mere examples, and the dose should be determined from the conditions of the patient.

The present invention is used when the use of compounds which have thrombopoietin receptor affinity and act as thrombopoietin receptor agonists are expected to improve pathological conditions. For example, hematological disorders accompanied by abnormal platelet count may be mentioned. Specifically, it is effective for therapy or prevention of human and mammalian diseases caused by abnormal megakaryopoiesis, especially those accompanied by thrombocytopenia. Examples of such diseases include thrombocytopenia accompanying chemotherapy or radiotherapy of cancer, thrombocytopenia caused by bone marrow transplantation, surgery and serious infections, or gastrointestinal bleeding, but such diseases are not restricted to those mentioned. Typical thrombocytopenias such as aplastic anemia, idiopathic thrombocytopenic purpura, myelodysplastic syndrome and thrombopoietin deficiency are also targets of the agents of the present invention. The present invention may be used as a peripheral stem cell mobilizer, a megakaryoblastic or megakaryocytic leukemia cell differentiation inducer and a platelet increasing agent for platelet donors. In addition, potential applications include therapeutic angiogenesis based on differentiation and proliferation of vascular endothelial cells and endothelial progenitor cells, prevention and therapy of arteriosclerosis, myocardial infarction, unstable angina, peripheral artery occlusive disease, but there is no restriction.

Next, the process for producing a compound represented by the formula (2) will be described.

The compound represented by the formula (2) is produced by incubating a microorganism belonging to the *Basipetospora* genus and isolating the compound from the culture medium.

The microorganism belonging to the *Basipetospora* genus to be used in the present invention may be a variant such as a strain with higher productivity obtained by inducing mutation in a microorganism or a strain obtained by transformation of a heterologous or homologous host using an appropriate vector such as a plasmid carrying a gene associated with the reaction which produces the compound from cells of a strain.

Preferred microorganisms belonging to the *Basipetospora* genus are strains of *Basipetospora* sp., and *Basipetospora* sp. strain No. 1142 is particularly preferred.

*Bacteriological* characteristics of *Basipetospora* sp. strain No. 1142 are as follows.
1. Viability in various media
Viability at 25° C. after 7 days of incubation

| | |
|---|---|
| Oatmeal agar medium | + |
| Malt extract agar medium | + |
| Potato dextrose agar medium | + |
| Viability at 37° C. | − |
| Production and secretion of soluble dye | − |

Colony morphology: diameter 37-42 cm, white and wooly, smooth, white bottoms
2. Morphological characteristics under a microscope
Hyphae: 1-5 μm wide, colorless, smooth and branched, septate
Conidiophores: upright, monogenetic
Conidiogenous cells: linear, nonannular ends
Conidia: connected in chains, unicellular, spherical to subspherical, rough surface, from 7 to 12 μm in diameter On the basis of the above-mentioned characteristics, Strain No. 1142 was classified into the genus *Basipetospora*, in comparison with known strains, and designated as *Basipetospora* sp. strain No. 1142. It was deposited as follows.
The International Patent Organism Depositary (IPOD), the National Institute of Advanced Industrial Science and Technology,
Chuo 6, 1-1-1, Higashi, Tsukuba-shi, Ibaraki, Japan, 305-8566
Jul. 22, 2002 (22.07.2002), 14 Sanseiki, No. 990 (FERM P-18940)
Accession Number: IPOD FERM BP-8410

*Basipetospora* sp. strain No. 1142 is likely to change its characteristics, like other mold fungi. For example, any mutants (spontaneous or induced), transformants or genetic recombinants of or originated from strain No. 1142 may be used in the present invention as long as they produce xanthocillin X monomethyl ether (the compound wherein $R^5$=H, $R^6$=H, $R^7$=CH$_3$, $R^8$=H and $R^b$=H), xanthocillin X dimethyl ether (the compound wherein $R^5$=CH$_3$, $R^6$=H, $R^7$=CH$_3$, $R^8$=H and $R^b$=H), 3-methoxyxanthocillin X dimethyl ether (the compound wherein $R^5$=CH$_3$, $R^6$=H, $R^7$=CH$_3$, $R^8$=OCH$_3$ and $R^b$=H) or 3,3'-dimethoxyxanthocillin X dimethyl ether (the compound wherein $R^5$=CH$_3$, $R^6$=H, $R^7$=CH$_3$, $R^8$=OCH$_3$ and $R^b$=OCH$_3$).

The method of incubating a microorganism of *Basipetospora* sp. will be described.

In the present invention, to obtain the compound represented by the formula (2), a microorganism of *Basipetospora* sp. is incubated in a culture medium. Known nutrients conventionally used for incubation of mold fungi may be used. For example, the carbon source may, for example, be glucose, sucrose, starch syrup, starch, dextrin, soybean oil, and the nitrogen source may, for example, be peptone, broth, yeast extract, corn steep liquor, oatmeal, ammonium sulfate, ammonium chloride, ammonium nitrate or urea. If necessary, inorganic salts such as sodium chloride, magnesium sulfate, copper sulfate, zinc sulfate, manganese chloride, calcium carbonate and phosphate salts may be added singly or in combination. In addition, organic substances which promote growth of the strain or production of the compound represented by the formula (2) such as nucleic acids, vitamins and inorganic substances may be arbitrarily added. When foaming of the culture remarkable, an antifoam agent may be added.

As the incubation method, incubation with shaking or with stirring and aeration under aerobic conditions is most suitable. The incubation temperature is preferably from 20 to 28° C., and the culture medium is preferably adjusted to pH 5.0-8.0. As to the incubation time, it is preferred to continue the incubation usually for 8 to 16 days until the accumulation of the compounds represented by the formula (2) in the culture medium or the cells reaches a maximum. Suitable incubation conditions may be selected depending on the characteristics of the strain to be used and the incubation method.

The methods of isolation and purification of the compounds represented by the formula (2) will be described. After the incubation, the compounds represented by the formula (2) is isolated and purified from the culture medium by ordinary methods for isolation of microbial metabolites from the culture. Namely, vacuum concentration, freeze drying, extraction with organic solvents such as butanol, ethyl acetate, chloroform and benzene, various kinds of ion exchange chromatography, gel permeation chromatography using Sephadex LH-20 and the like, adsorption chromatography using activated carbon, silica gel and the like, absorption and desorption of active substances by thin layer chromatography and high performance liquid chromatography using reversed-phase columns may be employed singly or in appropriate combinations or repeatedly to isolate the compounds represented by the formula (2). The physical and chemical properties of some of the compounds represented by the formula (2) are shown below.

Xanthocillin X monomethyl ether (the compound wherein $R^5$=H, $R^6$=H, $R^7$=CH$_3$, $R^8$=H and $R^b$=H)
1. Molecular weight: 302
2. Composition formula: $C_{19}H_{14}N_2O_2$
3. Properties and color: yellow neutral substance in the form of needle crystals
4. $^1$H Nuclear magnetic resonance spectrum: The chemical shifts (δ) measured by proton nuclear magnetic resonance spectroscopy in deuteriochloroform are shown below.
δ (ppm): 7.79 (2H, d), 7.72 (2H, d), 7.02 (2H, d), 7.01 (1H, s), 6.87 (1H, s), 6.86 (2H, d), 3.85 (3H, s)
5. $^{13}$C Nuclear magnetic resonance spectrum: The chemical shifts (δ) measured by carbon nuclear magnetic resonance spectroscopy in deuteriochloroform are shown below.
δ (ppm): 48.0, 114.1, 115.2, 115.6, 116.1, 123.6, 126.9, 127.7, 131.4, 131.7, 159.8, 161.4, 173.4, 173.5
6. Mass spectrum: (EI-MS)m/z=302 (M$^+$) Xanthocillin X dimethyl ether (the compound wherein $R^5$=CH$_3$, $R^6$=H, $R^7$=CH$_3$, $R^8$=H and $R^b$=H)

1. Molecular weight: 316
2. Composition formula: $C_{20}H_{16}N_2O_2$
3. Properties and color: yellow neutral substance in the form of needle crystals
4. $^1H$ Nuclear magnetic resonance spectrum: The chemical shifts ($\delta$) measured by proton nuclear magnetic resonance spectroscopy in deuteriochloroform are shown below.
δ (ppm): 7.79 (4H, d), 7.02 (2H, d), 6.98 (4H, d), 3.87 (6H, s)
5. $^{13}C$ Nuclear magnetic resonance spectrum: The chemical shifts ($\delta$) measured by carbon nuclear magnetic resonance spectroscopy in deuteriochloroform are shown below.
δ (ppm): 55.5, 114.5, 116.3, 124.9, 127.5, 131.8, 161.2, 173.3
6. Mass spectrum: (EI-MS)m/z=316 (M$^+$) 3-Methoxyxanthocillin X dimethyl ether (the compound wherein $R^5$=CH$_3$, $R^6$=H, $R^7$=CH$_3$, $R^8$OCH$_3$ and $R^b$=H)
1. Molecular weight: 346
2. Composition formula: $C_{21}H_{18}N_2O_3$
3. Properties and color: brown neutral substance
4. $^1H$ Nuclear magnetic resonance spectrum: The chemical shifts ($\delta$) measured by proton nuclear magnetic resonance spectroscopy in deuteriochloroform are shown below.
δ (ppm): 7.79 (2H, s), 7.49 (H, d), 7.36 (H, dd), 7.03 (H, s), 7.02 (H, s), 6.99 (2H, d), 6.95 (H, d), 3.96 (3H, s), 3.95 (3H, s), 3.88 (3H, s)
5. $^{13}C$ Nuclear magnetic resonance spectrum: The chemical shifts ($\delta$) measured by carbon nuclear magnetic resonance spectroscopy in deuteriochloroform are shown below.
δ (ppm): 55.5, 56.1, 111.2, 111.9, 114.5, 116.3, 116.2, 124.6, 124.9, 125.1, 127.6, 127.8, 131.8, 149.1, 150.9, 161.2, 173.3, 173.5
6. Mass spectrum: (EI-MS)m/z=346 (M$^+$) 3,3'-Dimethoxyxanthocillin X dimethyl ether (the compound wherein $R^5$=CH$_3$, $R^6$=H, $R^7$=CH$_3$, $R^8$=OCH$_3$ and $R^b$=OCH$_3$)
1. Molecular weight: 376
2. Composition formula: $C_{22}H_{20}N_2O_4$
3. Properties and color: brown neutral substance
4. $^1H$ Nuclear magnetic resonance spectrum: The chemical shifts ($\delta$) measured by proton nuclear magnetic resonance spectroscopy in deuteriochloroform are shown below.
δ (ppm): 7.79 (2H, d), 7.08 (2H, s), 7.05 (H, s), 7.00 (H, s), 6.99 (2H, d), 3.92 (9H, s), 3.87 (3H, s)
5. $^{13}C$ Nuclear magnetic resonance spectrum: The chemical shifts ($\delta$) measured by carbon nuclear magnetic resonance spectroscopy in deuteriochloroform are shown below.
δ (ppm): 55.5, 56.2, 61.1, 107.4, 114.6, 116.0, 117.5, 124.7, 127.5, 127.8, 128.3, 132.0, 140.1, 153.3, 161.4, 173.5, 173.9
6. Mass spectrum: (EI-MS)m/z=376 (M$^+$)

Now, production of the compounds represented by the formula (1) will be described.

The compounds represented by the formula (1) are obtainable using microorganisms, by chemical modification of microbially produced compounds, or by chemical synthesis.

The compound wherein $R^1$=H, $R^2$=H, $R^3$=H, $R^4$=H and $R^a$=H (xanthocillin X) is obtainable using a microorganism such as *Penicillium* notatum or *Penicillium Chrysogenum* (GB 898498, Antibiotics Ann (1957) Volume Date 1956-57 140-3p and DE 1123087).

The compound wherein $R^1$=H, $R^2$=H, $R^3$=CH$_3$, $R^4$=H and $R^a$=H (xanthocillin X monomethyl ether) is obtainable using a microorganisms such as *Dichotomomyces albus* (J. Antibiotics 21, 582-587 (1968), J. Antibiotics 21 587-591 (1968)).

The compound wherein $R^1$=CH$_3$, $R^2$=H, $R^3$=CH$_3$, $R^4$=H and $R^a$=H (xanthocillin X dimethyl ether), the compound wherein $R^1$=C$_2$H$_5$, $R^2$=H, $R^3$=C$_2$H$_5$, $R^4$=H and $R^a$=H (xanthocillin X diethyl ether) and the compound wherein $R^1$=CH$_3$, $R^2$=H, $R^3$=CH$_3$, $R^4$=OCH$_3$ and $R^a$=H (3-methoxyxanthocillin X dimethyl ether) are obtainable using a microorganisms such as *Aspergullus* sp. (Strain No. 208 or No. 98) (J. Antibiotics 21 (12) 671-679 (1968)).

The compound wherein $R^1$=H, $R^2$=OH, $R^3$=H, $R^4$=H and $R^a$=H (xanthocillin Y1) and the compound wherein $R^1$=H, $R^2$=OH, $R^3$=H, $R^4$=OH and $R^a$=H (xanthocillin Y2) are obtainable using a microorganism such as *Penicillium* notatum (Chem. Ber 105 (9), 3061 (1972)).

The compound wherein $R^1$=CH$_3$, $R^2$=H, $R^3$=SO$_3$H, $R^4$=H and $R^a$=H (xanthocillin X monomethyl ether sulfate ester) is obtainable using a microorganism such as *Aspergillus* sp. (No. FA2692) (J. Antibiotics 46 687-688 (1993)).

Among the compounds represented by the formula (1), the following compounds are obtained by chemical modification of microbially produced compounds.

The compounds wherein $R^1$=CH$_3$, $R^2$=H, $R^4$=H, $R^a$=H and $R^3$ is an alkyl group, an alkylcarbonyl group or an arylcarbonyl group are obtainable from the xanthocillin X monomethyl ether by the method disclosed in JP-A-2-304058.

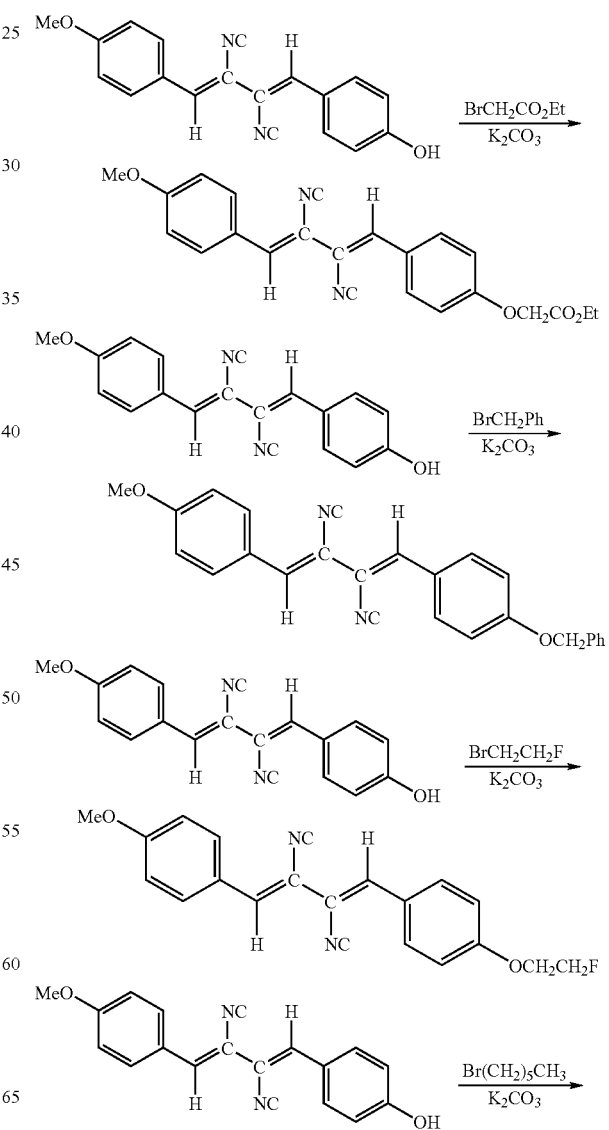

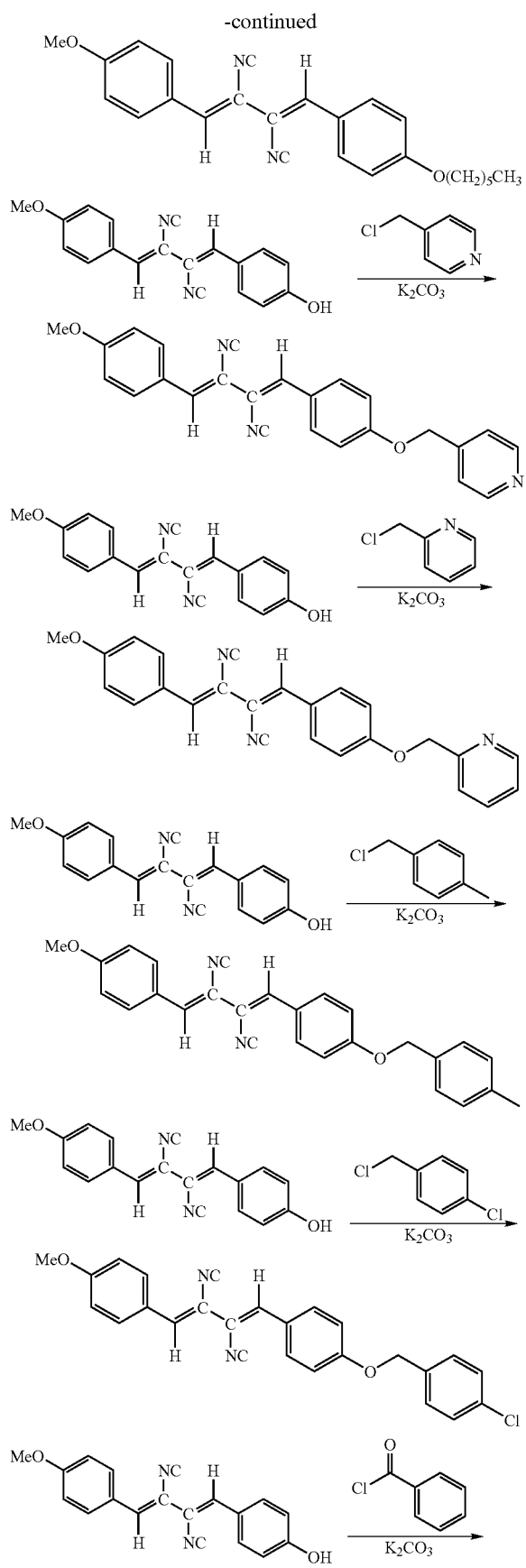

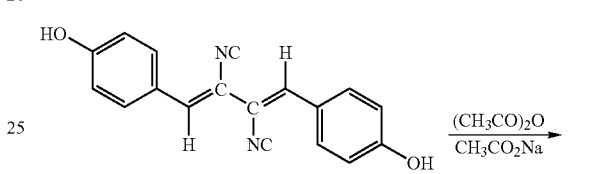

Namely, they are obtainable by reacting the corresponding halide with xanthocillin X monomethyl ether in the presence of a base such as $K_2CO_3$.

The compounds wherein $R^2$=H, $R^4$=H, $R^a$=H, and $R^1$ and $R^3$ are alkylcarbonyl groups or arylcarbonyl groups are obtainable from xanthocillin X by the method disclosed in Pharmazie 12, 567-580 (1957).

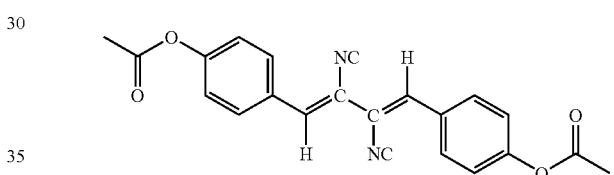

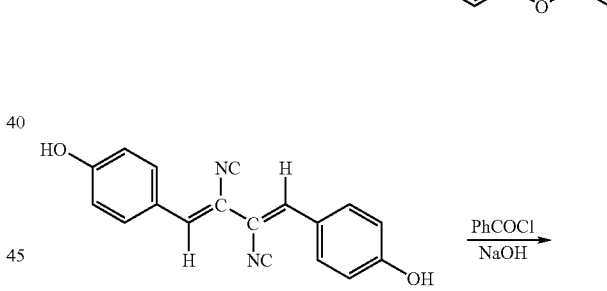

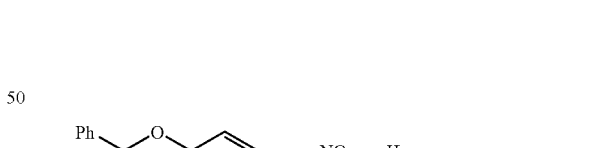

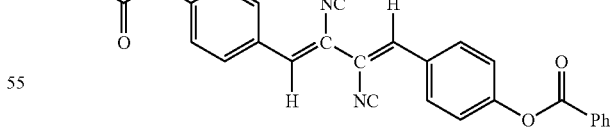

Namely, they are obtainable by reacting the corresponding acid anhydride or acyl halide with xanthocillin X in the presence of an appropriate base.

The compounds wherein $R^2$=H, $R^4$=H, $R^a$=H, and $R^1$ and $R^3$ are alkyl groups substituted by dialkylamino groups are obtainable from xanthocillin X by the method disclosed in DE 11658.

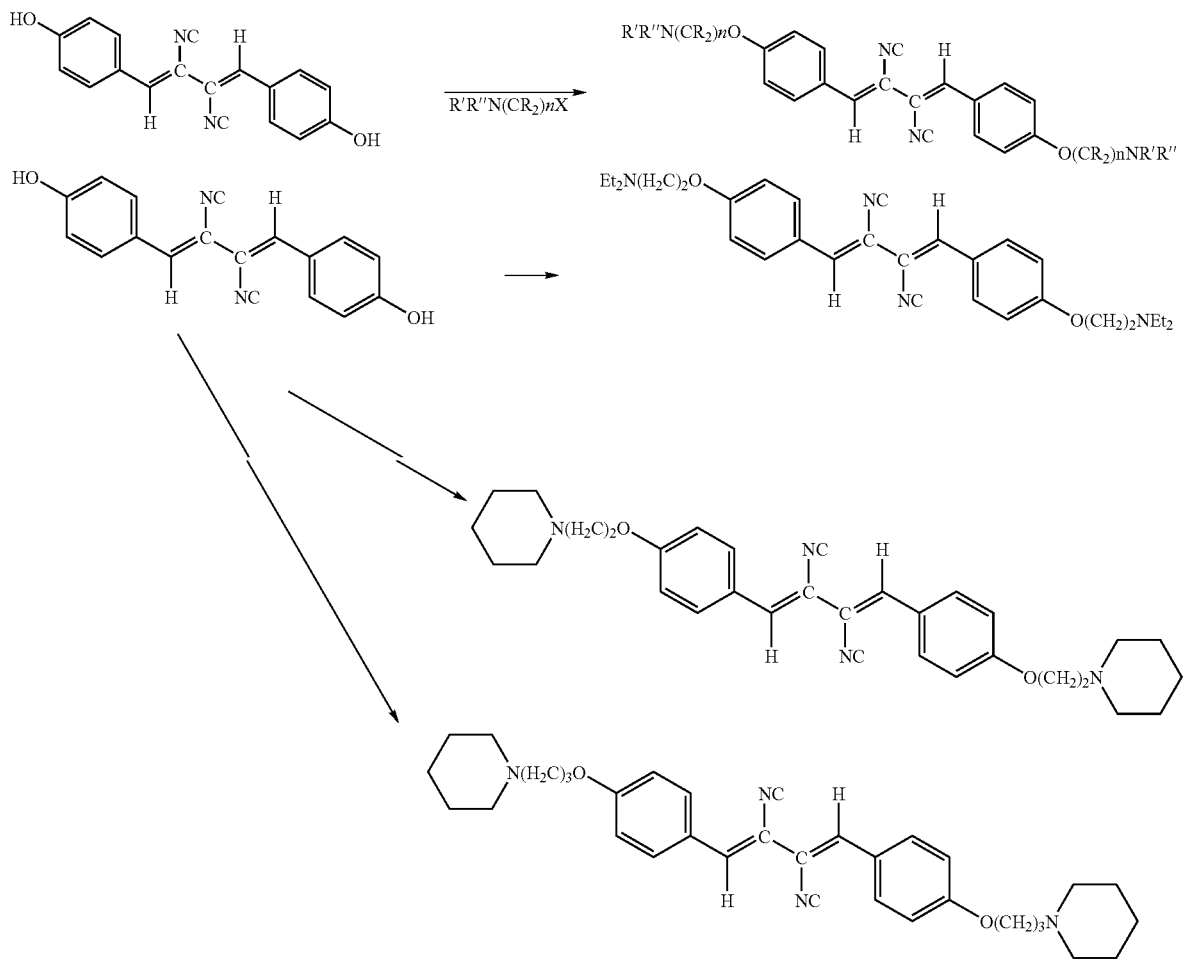

Namely, they are obtainable by reacting the corresponding halide with xanthocillin X.

The compounds wherein $R^2$=H, $R^4$=H, $R^a$=H, and $R^1$ and $R^3$ are alkyl groups, the compounds wherein $R^2$ is an alkoxy group, $R^4$=H, $R^a$=H, and $R^1$ and $R^3$ are alkyl groups, and the compounds wherein $R^a$=H, $R^2$ and $R^4$ are alkoxy groups, and $R^1$ and $R^3$ are alkyl groups are obtainable from xanthocillin X, xanthocillin Y1 or xanthocillin Y2, respectively, by the method disclosed in Chem Ber 105 (9) 3061 (1972).

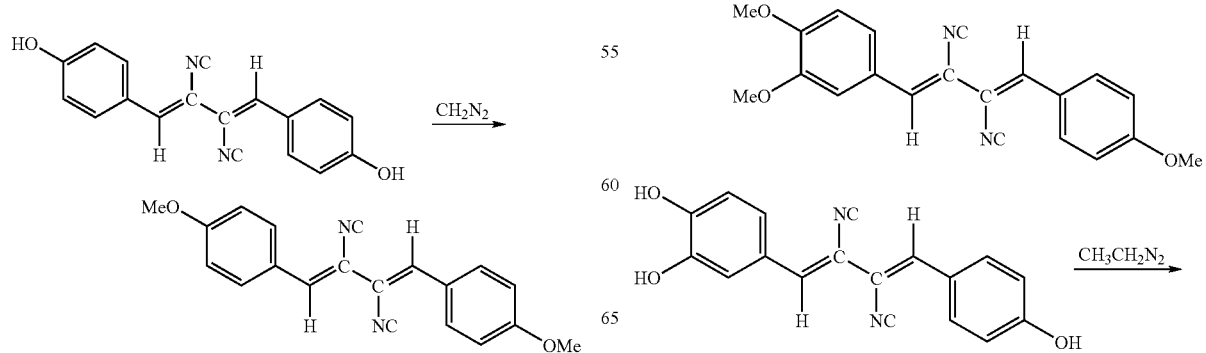

-continued

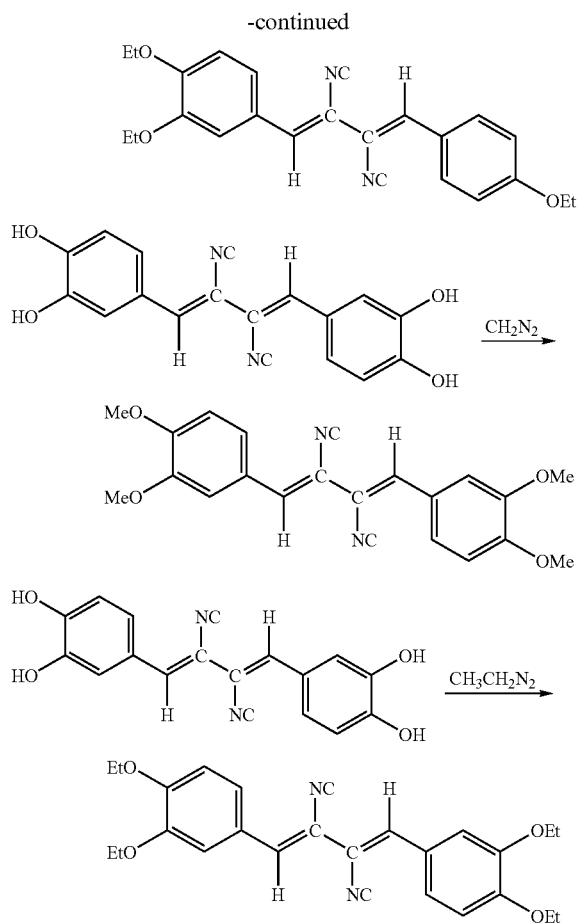

Namely, they are obtainable by reacting the corresponding diazoalkyl with xanthocillin X, xanthocillin Y1 or xanthocillin Y2, respectively.

Among the compounds represented by the formula (1), the compound wherein $R^1$=$CH_3$, $R^2$=H, $R^3$=$CH_3$, $R^4$=H and $R^a$=H (xanthocillin X dimethyl ether) is obtainable by chemical synthesis (Angew Chem 74, 215 (1962), Chem Ber 98 (1) 193-201 (1965) and DE 1167332).

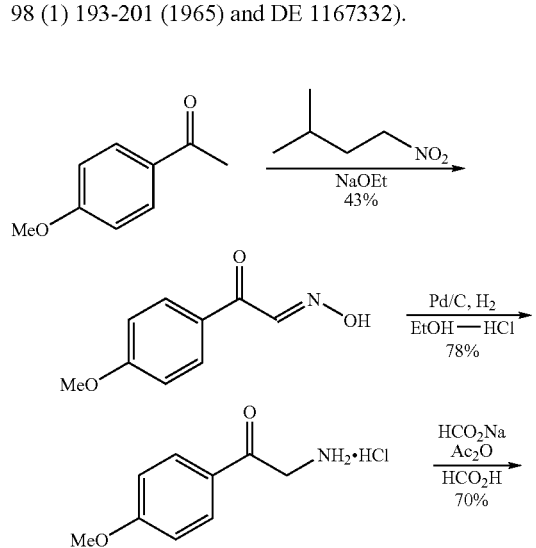

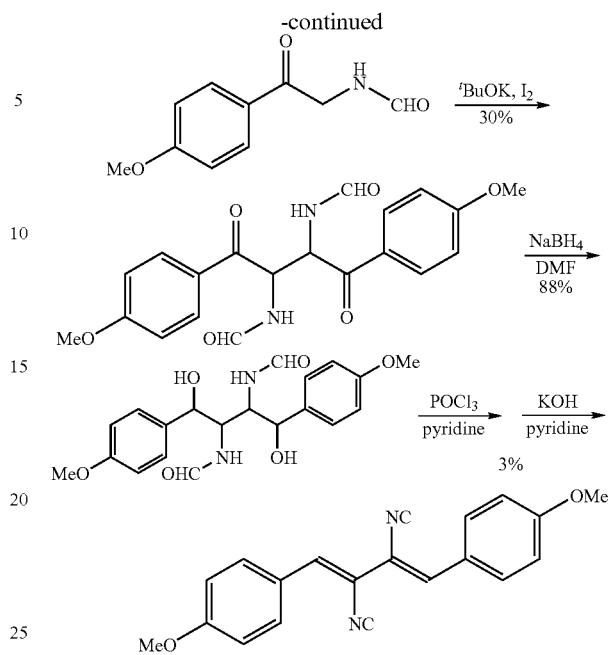

EXAMPLES

Now, the present invention will be described in further detail by reference to Examples. However, it should be understood that the present invention is by no means restricted to these specific Examples.

Preparation Example 1

100 ml of a liquid medium (composition; soluble starch 2%, glucose 0.5%, polypeptone 0.2%, corn steep liquor 0.5%) was poured into a 500 ml Erlenmeyer flask and sterilized by autoclaving at 120° C. for 20 minutes, then inoculated with a loopful of strain No. 1142 of the *Basipetospora* genus and incubated at 25° C. for 4 days with rotation at 140 rpm. The resulting culture was transferred to 1 l of the same culture medium as mentioned above in 5 l Erlenmeyer flasks (18 flasks sterilized by autoclaving) and incubated at 25° C. for 7 days with rotation at 140 rpm. After incubation, the resulting culture was filtered to give cells and a filtrate.

The cells were extracted with 5 l of 80% aqueous acetone, and the cells were removed by filtration to obtain a cell extract. The cell extract was concentrated by removing the solvent in vacuo, and 0.5 l of hexane was added. The resulting aqueous layer was extracted with 0.5 l of ethyl acetate three times, and the ethyl acetate layer was concentrated in vacuo to give about 771 mg of a brown oil. The oil was separated by silica gel chromatography (2.5×28 cm) using chloroform-methanol (100:0-5) as the developing solvent, and each fraction was concentrated to dryness. Thus, yellow active fraction A (about 33 mg) containing xanthocillin X monomethyl ether and yellow active fraction B (about 37 mg) containing xanthocillin X dimethyl ether were obtained.

Crystallization of active fraction B from chloroform-hexane gave yellow needle crystals of xanthocillin X dimethyl ether (about 30 mg). Active fraction A was separated by silica gel chromatography (2.5×28 cm) using chloroform-methanol (3:1-3) as the developing solvent, and each fraction was concentrated to dryness. Thus, active fraction (about 11 mg)

containing xanthocillin X monomethyl ether was obtained. Crystallization of this fraction from chloroform-hexane gave yellow needle crystals of xanthocillin X monomethyl ether (about 10 mg).

The physical and chemical properties of the compounds thus obtained are shown below.
1) The physical and chemical properties of the xanthocillin X monomethyl ether:
1. Molecular weight: 302
2. Composition formula: $C_{19}H_{14}N_2O_2$
3. Properties and color: yellow neutral substance in the form of needle crystals
4. $^1H$ Nuclear magnetic resonance spectrum: The chemical shifts (δ) measured by proton nuclear magnetic resonance spectroscopy in deuteriochloroform are shown below.
δ (ppm): 7.79 (2H, d), 7.72 (2H, d), 7.02 (2H, d), 7.01 (1H, s), 6.87 (1H, s), 6.86 (2H, d), 3.85 (3H, s)
5. $^{13}C$ Nuclear magnetic resonance spectrum: The chemical shifts (δ) measured by carbon nuclear magnetic resonance spectroscopy in deuteriochloroform are shown below.
δ (ppm): 48.0, 114.1, 115.2, 115.6, 116.1, 123.6, 126.9, 127.7, 131.4, 131.7, 159.8, 161.4, 173.4, 173.5
6. Mass spectrum: (EI-MS)m/z=302 ($M^+$)
2) The physical and chemical properties of the xanthocillin X dimethyl ether:
1. Molecular weight: 316
2. Composition formula: $C_{20}H_{16}N_2O_2$
3. Properties and color: yellow neutral substance in the form of needle crystals
4. $^1H$ Nuclear magnetic resonance spectrum: The chemical shifts (δ) measured by proton nuclear magnetic resonance spectroscopy in deuteriochloroform are shown below.
δ (ppm): 7.79 (4H, d), 7.02 (2H, d), 6.98 (4H, d), 3.87 (6H, s)
5. $^{13}C$ Nuclear magnetic resonance spectrum: The chemical shifts (δ) measured by carbon nuclear magnetic resonance spectroscopy in deuteriochloroform are shown below.
δ (ppm): 55.5, 114.5, 116.3, 124.9, 127.5, 131.8, 161.2, 173.3
6. Mass spectrum: (EI-MS)m/z=316 ($M^+$)

Preparation Example 2

100 ml of a liquid medium (composition; soluble starch 2%, glucose 0.5%, yeast extract 0.2%, magnesium phosphate 1%, defatted soybean 1%) was poured into a 500 ml Erlenmeyer flask and sterilized by autoclaving at 120° C. for 20 minutes, then inoculated with a loopful of strain No. 1142 of the *Basipetospora* genus and incubated at 25° C. for 4 days with rotation at 140 rpm. The resulting culture was transferred to 0.9 l of the same culture medium as mentioned above in 5 l Erlenmeyer flasks (5 flasks sterilized by autoclaving) and incubated at 25° C. for 11 days with rotation at 140 rpm. After incubation, the resulting culture was filtered to give cells and a filtrate.

The cells were extracted with 1.5 l of 80% aqueous acetone, and the cells were removed by filtration to obtain a cell extract. The cell extract was concentrated by removing the solvent in vacuo, and 0.4 l of hexane was added. The resulting aqueous layer was extracted with 0.8 l of ethyl acetate three times, and the ethyl acetate layer was concentrated in vacuo to give about 608 mg of a brown oil. The oil was separated by silica gel chromatography (2.5×28 cm) using chloroform-methanol (100:0-5) as the developing solvent, and each fraction was concentrated to dryness. Thus, a brown active fraction (about 34 mg) containing 3-methoxyxanthocillin X dimethyl ether and 3,3'-dimethoxyxanthocillin X dimethyl ether was obtained.

This fraction was dissolved in acetonitrile and separated by $C_{18}$ reversed phase preparative HPLC (eluent; 75 aqueous acetonitrile, elution rate; 15 ml/min, absorptiometric detector, column; Inertsil PREP-ODS 20×250 mm, column temperature; 40° C.) to obtain a fraction with a retention time of 13.3 to 14.0 minutes. The fraction with a retention time of 13.3 to 14.0 minutes was concentrated to dryness, dissolved in acetonitrile and purified by reversed phase preparative HPLC (eluent; 65% aqueous acetonitrile, elution rate; 15 ml/min, absorptiometric detector, column; Inertsil PREP-ODS 20×250 mm, column temperature; 40° C.) to obtain two fractions with retention times of 25.4 minutes and 27.4 minutes. The fractions with retention times of 25.4 minutes and 27.4 minutes were concentrated to dryness, respectively, to give 3-methoxyxanthocillin X dimethyl ether (about 3.6 mg) as a brown substance and 3,3'-dimethoxyxanthocillin X dimethyl ether (about 5.5 mg) as a brown substance.

The physical and chemical properties of the compounds thus obtained are shown below.
1) The physical and chemical properties of the 3-methoxyxanthocillin X dimethyl ether:
1. Molecular weight: 346
2. Composition formula: $C_{21}H_{18}N_2O_3$
3. Properties and color: brown neutral substance
4. $^1H$ Nuclear magnetic resonance spectrum: The chemical shifts (δ) measured by proton nuclear magnetic resonance spectroscopy in deuteriochloroform are shown below.
δ (ppm): 7.79 (2H, s), 7.49 (H, d), 7.36 (H, dd), 7.03 (H, s), 7.02 (H, s), 6.99 (2H, d), 6.95 (H, d), 3.96 (3H, s), 3.95 (3H, s), 3.88 (3H, s)
5. $^{13}C$ Nuclear magnetic resonance spectrum: The chemical shifts (δ) measured by carbon nuclear magnetic resonance spectroscopy in deuteriochloroform are shown below.
δ (ppm): 55.5, 56.1, 111.2, 111.9, 114.5, 116.3, 116.2, 124.6, 124.9, 125.1, 127.6, 127.8, 131.8, 149.1, 150.9, 161.2, 173.3, 173.5
6. Mass spectrum: (EI-MS)m/z=346 ($M^+$)
2) The physical and chemical properties of the 3,3'-dimethoxyxanthocillin X dimethyl ether
1. Molecular weight: 376
2. Composition formula: $C_{22}H_{20}N_2O_4$
3. Properties and color: brown neutral substance
4. $^1H$ Nuclear magnetic resonance spectrum: The chemical shifts (δ) measured by proton nuclear magnetic resonance spectroscopy in deuteriochloroform are shown below.
δ (ppm): 7.79 (2H, d), 7.08 (2H, s), 7.05 (H, s), 7.00 (H, s), 6.99 (2H, d), 3.92 (9H, s), 3.87 (3H, s)
5. $^{13}C$ Nuclear magnetic resonance spectrum: The chemical shifts (δ) measured by carbon nuclear magnetic resonance spectroscopy in deuteriochloroform are shown below.
δ (ppm): 55.5, 56.2, 61.1, 107.4, 114.6, 116.0, 117.5, 124.7, 127.5, 127.8, 128.3, 132.0, 140.1, 153.3, 161.4, 173.5, 173.9
6. Mass spectrum: (EI-MS)m/z=376 ($M^+$)

Assay Example 1

Stimulation of Proliferation of a Thrombopoietin (TPO)-Dependent Cell Line (1)

(1) Cells and Cell Culture

The reactivity of a compound of the present invention, xanthocillin X monomethyl ether, with thrombopoietin (TPO) receptor was assayed using a human leukemic cell line, UT7/EPO-mpl. UT7/EPO-mpl is a stable transformed cell line obtained by introducing into human leukemic cell line UT7/EPO a vector that induces expression of human TPO receptor (c-mpl) under control of a cytomegaloviral promoter by the method of Takatoku et al. (J. Biol. Chem., 272:7259-7263 (1997)). Proliferation of this cell line is stimulated by TPO, while its mother cell line UT7/EPO exhibits no response to TPO. These two cell lines were subcultured in IMDM (GIBCO) containing 10% fetal bovine serum (FBS; TRACE SCIENTIFIC) using a $CO_2$ incubator (5% $CO_2$, 37° C.).

(2) Cell Proliferation Assay by the MTT Method

Figure 2:
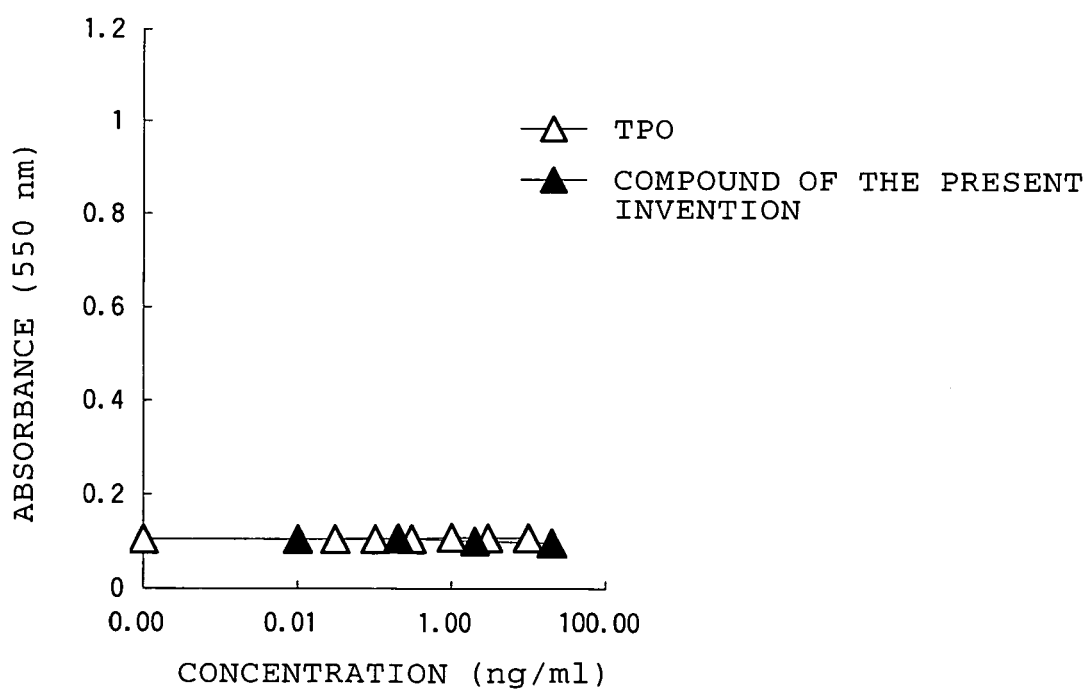
FIG. 2: Evaluation of the effect of the compound of the present invention (xanthocillin X monomethyl ether) on the proliferation of UT7/EPO cells by the MTT assay.

The subcultured cells described above were washed twice with PBS and suspended in IMDM containing 10% FBS at a cell density of $6 \times 10^4$ cells/ml. The cell suspension was transferred to a 96-well tissue culture plate (CORNING) in 100-μl aliquots. Then, xanthocillin X monomethyl ether dissolved in DMSO was diluted 83-fold with IMDM containing 10% FBS and added to the aforementioned cell suspension in 20-μl aliquots. The suspension was incubated in a $CO_2$ incubator (5% $CO_2$, 37° C.) for 4 days. Cell proliferation was assayed according to the method of Mosmann et al. (J. Immunological Methods, 65:55-63 (1983)). A 10-μl aliquot of 5 mg/ml MTT reagent (SIGMA) was added to each well of the tissue culture plate and the plate was incubated at 37° C. for 4 h. The formazan pigment generated was dissolved by adding 150 μl per well of 0.1 M/L HCl/isopropanol solution and the absorbance of the resulting pigment solution was measured at 550 nm with a 96-well microplate reader (BIO-RAD, M450). FIG. 1 shows the results with UT7/EPO-mpl cells, while FIG. 2 shows data obtained with UT7/EPO cells expressing no TPO receptor.

Assay Example 2

Activity of Signal Transduction Mediated by TPO Receptor

The signal-transducing activity of a compound of the present invention, xanthocillin X monomethyl ether, mediated by TPO receptor was assayed according to the method of Komatsu et al. (Blood, 87:4552-4560 (1996)). Human leukemic cell line UT7/EPO-mpl was washed three times with PBS and suspended in IMDM containing 10% FBS at a cell density of $9 \times 10^5$ cells/ml. The cell suspension was incubated in a $CO_2$ incubator (5% $CO_2$, 37° C.) for 18 h. To 2 ml of this cell suspension ($7 \times 10^6$ cells/ml), either TPO (final concentration, 30 ng/ml) or a DMSO solution of xanthocillin X monomethyl ether (final concentration, 1 μg/ml) was added. After incubating the mixture at 37° C. for 1-15 min, the cells were lysed in 1.4 ml of TNE buffer (20 mM Tris-HCl buffer (pH 7.4) containing 150 mM NaCl, 1 mM EDTA, 1% Triton X-100, 1 mM PMSF, 1 mM $Na_3VO_4$, and 1/400-diluted Protease Inhibitor Cocktail (SIGMA)). The cell lysate was centrifuged to collect the supernatant for immunoprecipitation with antibodies against proteins involved in signal transduction (anti-Jak2 (UPSTATE BIOTECHNOLOGY), anti-Tyk2 (UPSTATE BIOTECHNOLOGY), anti-STAT3 (SANTA CRUZ BIOTECHNOLOGY), anti-STAT5A (UPSTATE BIOTECHNOLOGY) and anti-PLCγ1 (UPSTATE BIOTECHNOLOGY)) and protein G Sepharose (PHARMACIA). The immunoprecipitated protein fraction was collected and denatured in a sample buffer for separation by SDS-polyacrylamide gel electrophoresis (7.5%). The separated proteins were transferred onto PVDF membrane (ATTO, 0.2 μm) at 100 V for 1 h for detection of tyrosine phosphorylation using an alkaline phosphatase-labeled antibody against phosphorylated tyrosine (RC20, TRANSDUCTION LABORATORIES). The antigen-antibody complex formed on the PVDF membrane was visualized with 150 μg/ml NBT (BIO-RAD) and 300 μg/ml BCIP (BIO-RAD). The results are summarized in Table 1.

TABLE 1

|  | DMSO | Xanthocillin X monomethyl ether | TPO |
|---|---|---|---|
| Jak2 | − | + | + |
| Tyk2 | − | + | + |
| STAT 3 | − | + | + |
| STAT 5A | − | + | + |
| PLCγ1 | − | + | + |

FIG. 1 demonstrated that proliferation of TPO-responsive UT7/EPO-mpl cells was stimulated by xanthocillin X monomethyl ether in a concentration-dependent manner, while no effect of this compound on proliferation was observed with UT7/EPO, the mother cell line, as shown in FIG. 2. These results indicate that the compound of the present invention, xanthocillin X monomethyl ether, acts on the TPO receptor selectively as an activator.

Table 1 shows that xanthocillin X monomethyl ether stimulates phosphorylation of Jak2, Tyk2, STAT3, STAT5A and PLCγ1 in the same manner as TPO does. The results demonstrate that the compound of the present invention shows agonistic action through the same signal transduction as that caused by TPO.

Assay Example 3

Stimulation of Proliferation of a Thrombopoietin (TPO)-Dependent Cell Line (2)

The reactivity of a compound of the present invention, 3-methoxyxanthocillin X dimethyl ether, with thrombopoietin (TPO) receptor was assayed using a human leukemic cell line, UT7/EPO-mpl.

Figure 3:
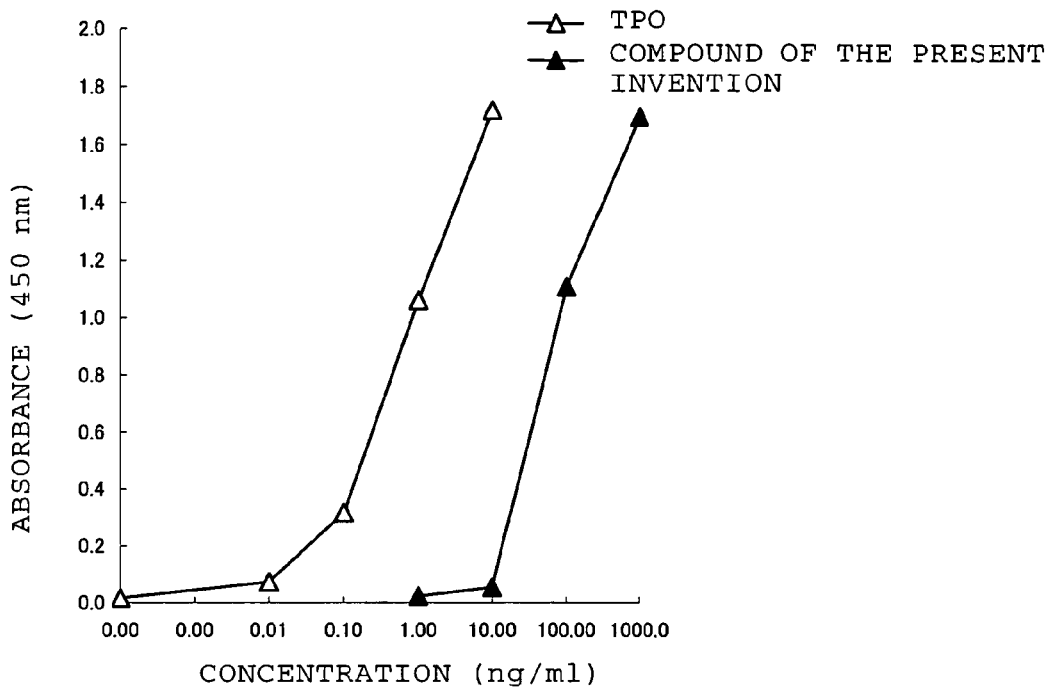
FIG. 3: Evaluation of the effect of the compound of the present invention (3-methoxyxanthocillin X dimethyl ether) on the proliferation of UT7/EPO-mpl cells by the WST assay.

Cells subcultured in the same manner as in Assay Example 1(1) were washed twice with PBS and suspended in IMDM containing 10% FBS at a cell density of $6 \times 10^4$ cells/ml. The cell suspension was transferred to a 96-well tissue culture plate (CORNING) in 100-μl aliquots. Then, 3-methoxyxanthocillin X dimethyl ether dissolved in DMSO was diluted 83-fold with IMDM containing 10% FBS and added to the aforementioned cell suspension in 20-μl aliquots. The suspension was incubated in a $CO_2$ incubator (5% $CO_2$, 37° C.) for 4 days. Cell proliferation was assayed using WST-8 reagent (Kishida Chemical Co., Ltd.) according to instructions by the manufacturer. A 10-μl aliquot of 5 mM WST-8 reagent solution was added to each well of the tissue culture plate, and the plate was incubated at 37° C. for 4 h. The formazan pigment generated was detected by measuring the absorbance at 450 nm with a 96-well microplate reader (Nihon Molecular Devices, Spectramax 190). FIG. 3 shows the results with UT7/EPO-mpl cells, while FIG. 4 shows data obtained with UT7/EPO cells expressing no TPO receptor.

Figure 4:
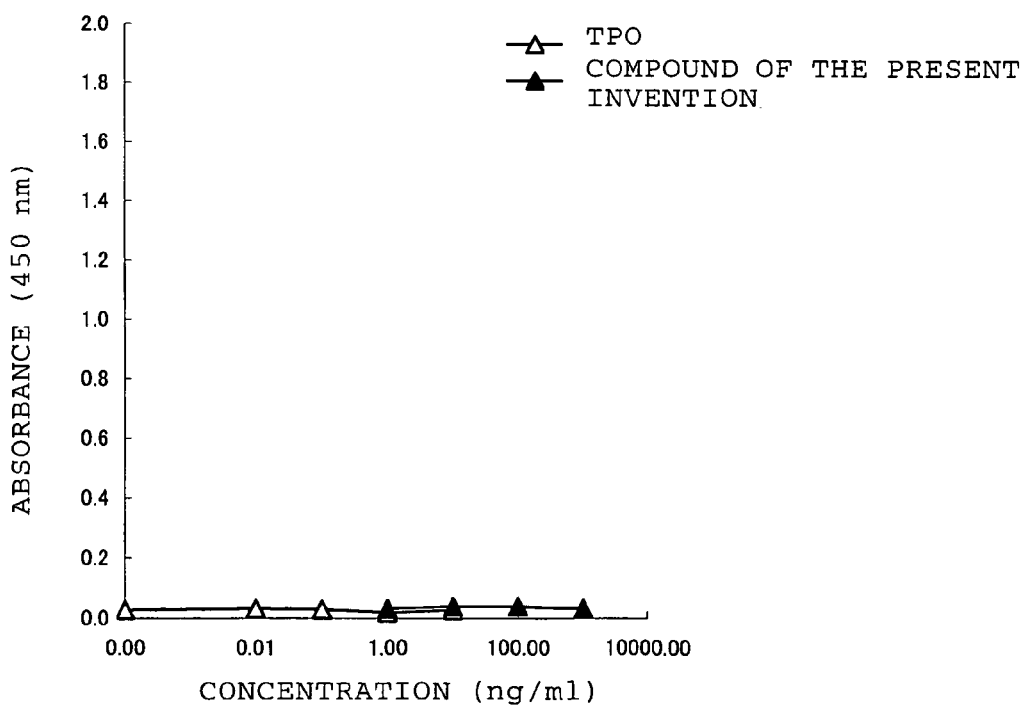
FIG. 4: Evaluation of the effect of the compound of the present invention (3-methoxyxanthocillin X dimethyl ether) on the proliferation of UT7/EPO cells by the WST assay.

FIG. 3 demonstrated that proliferation of TPO-responsive UT7/EPO-mpl cells was stimulated by 3-methoxyxanthocillin X dimethyl ether in a concentration-dependent manner, while no effect of this compound on proliferation was observed with UT7/EPO, the mother cell line, as shown in FIG. 4. These results indicate that the compound of the present invention, 3-methoxyxanthocillin X dimethyl ether, acts on the TPO receptor selectively as an activator.

Formulation Example 1

A granule preparation containing the following ingredients is prepared.

| Ingredients | |
|---|---|
| Compound represented by the formula (1) | 10 mg |
| Lactose | 700 mg |
| Corn Starch | 274 mg |
| HPC-L | 16 mg |
| | 1000 mg |

A compound represented by the formula (1) and lactose are sifted through a 60-mesh sieve. Corn starch is sifted though a 120-mesh sieve. They are mixed in a V-type blender. The powder mixture is kneaded with a low-viscosity hydroxypropylcellulose (HPC-L) aqueous solution, granulated (extrusion granulation, die size 0.5-1 mm) and dried. The resulting dry granules are sifted through a shaking sieve (12/60 mesh) to obtain a granule preparation.

Formulation Example 2

A powder preparation for capsulation containing the following ingredients is prepared.

| Ingredients | |
|---|---|
| Compound represented by the formula (1) | 10 mg |
| Lactose | 79 mg |
| Corn Starch | 10 mg |
| Magnesium Stearate | 1 mg |
| | 100 mg |

A compound represented by the formula (1) and lactose are sifted through a 60-mesh sieve. Corn starch is sifted though a 120-mesh sieve. They are mixed with magnesium stearate in a V-type blender. The 10% powder is put in hard capsules No. 5, 100 mg each.

Formulation Example 3

A granule preparation for capsulation containing the following ingredients is prepared.

| Ingredients | |
|---|---|
| Compound represented by the formula (1) | 15 mg |
| Lactose | 90 mg |
| Corn Starch | 42 mg |
| HPC-L | 3 mg |
| | 150 mg |

A compound represented by the formula (1) and lactose are sifted through a 60-mesh sieve. Corn starch is sifted though a 120-mesh sieve. They are mixed in a V-type blender. The powder mixture is kneaded with a low-viscosity hydroxypropylcellulose (HPC-L) aqueous solution, granulated and dried. The resulting dry granules are sifted through a shaking sieve (12/60 mesh). The granules are put in hard capsules No. 4, 150 mg each.

Formulation Example 4

A tablet preparation containing the following ingredients is prepared.

| Ingredients | |
|---|---|
| Compound represented by the formula (1) | 10 mg |
| Lactose | 90 mg |
| Microcrystalline cellulose | 30 mg |
| Magnesium Stearate | 5 mg |
| CMC-Na | 15 mg |
| | 150 mg |

A compound represented by the formula (1), lactose, microcrystalline cellulose and CMC-Na (carboxymethylcellulose sodium salt) are sifted through a 60-mesh sieve and mixed. The powder mixture is mixed with magnesium stearate to give a bulk powder mixture. The powder mixture is compressed directly into 150 mg tablets.

Formulation Example 5

An intravenous preparation is prepared as follows.

| | |
|---|---|
| Compound represented by the formula (1) | 100 mg |
| Saturated Fatty Acid Glyceride | 1000 ml |

Solutions having the above-mentioned composition are usually administered to a patient intravenously at a rate of 1 ml per 1 minute.

INDUSTRIAL APPLICABILITY

The compounds of the present invention which have affinity for thrombopoietin receptor and act as thrombopoietin receptor agonists are useful as preventive, therapeutic and improving agents for diseases against which activation of the thrombopoietin receptor is effective, especially as drugs for hematological disorders accompanied by abnormal platelet count and as drugs for diseases treated or prevented by stimulating differentiation and proliferation of vascular endothelial cells and endothelial progenitor cells, and are useful as medicines.

The invention claimed is:
1. A method of increasing platelets in a human having a disease selected from the group consisting of thrombocytopenia caused by bone marrow transplantation, thrombocytopenia caused by surgery, thrombocytopenia caused by infection, thrombocytopenia caused by gastrointestinal bleeding, aplastic anemia, idiopathic thrombocytopenic purpura, myelodysplastic syndrome, and thrombopoietin deficiency, the method comprising
administering an isolated compound or its salt to the human in need thereof in an amount sufficient to increase the platelets in the human in need thereof,
wherein the isolated compound or its salt is represented by the formula (1) or its salt,

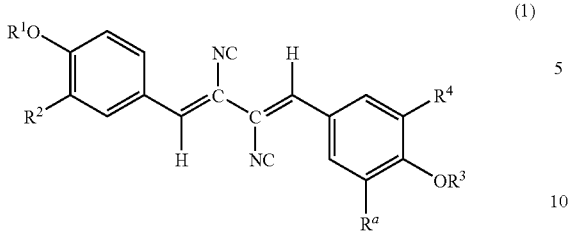

(1)

wherein each of $R^1$ and $R^3$ is independently a hydrogen atom, $SO_3H$, a $C_{1-6}$ alkyl group, a $C_{1-6}$ alkylcarbonyl group or a $C_{6-18}$ arylcarbonyl group, and wherein each of $R^2$, $R^4$ and $R^a$ is independently a hydrogen atom, a hydroxyl group or a $C_{1-6}$ alkoxy group;

wherein the $C_{1-6}$ alkyl group, the $C_{1-6}$ alkylcarbonyl group and the $C_{6-18}$ arylcarbonyl group may be optionally substituted with a halogen atom, a hydroxyl group, a $C_{2-6}$ alkenyl group, a $C_{1-6}$ alkoxy group, a $C_{1-6}$ alkoxycarbonyl group, a $C_{6-18}$ aryl group, a 2-pyridyl group, a 3-pyridyl group, a 4-pyridyl group, a 2-furanyl group, a 3-furanyl group, a 2-thienyl group, a 3-thienyl group or $NR^9R^{10}$, wherein the $C_{6-18}$ aryl group, the 2-pyridyl group, the 3-pyridyl group, the 4-pyridyl group, the 2-furanyl group, the 3-furanyl group, the 2-thienyl group and the 3-thienyl group may be optionally substituted with a halogen atom or a $C_{1-6}$ alkyl group, wherein each of $R^9$ and $R^{10}$ is independently a hydrogen atom or a $C_{1-6}$ alkyl group or $R^9$ and $R^{10}$ mean, together with each other, $—(CH_2)_nX(CH_2)_m—$, wherein the $C_{1-6}$ alkyl group may be optionally substituted with a $C_{6-18}$ aryl group wherein X is $CR^{11}R^{12}$, $NR^{13}$, O or S, wherein each of $R^{11}$ and $R^{12}$ is independently a hydrogen atom or a $C_{1-6}$ alkyl group, wherein $R^{13}$ is a hydrogen atom or a $C_{1-6}$ alkyl group that may be optionally substituted with a $C_{6-18}$ aryl group, wherein n is 1, 2 or 3, and m is 1, 2 or 3, provided that n+m is 3, 4 or 5, wherein the $C_{1-6}$ alkyl group may be optionally substituted with a $C_{6-18}$ aryl group, wherein $R^{13}$ is a hydrogen atom or a $C_{1-6}$ alkyl group, and wherein the $C_{1-6}$ alkyl group may be optionally substituted with a $C_{6-18}$ aryl group.

2. The method of claim 1, wherein in the isolated compound of or its salt that is administered to the human, each of $R^1$ and $R^3$ is independently a hydrogen atom, $SO_3H$, a $C_{1-6}$ alkyl group, a $C_{1-6}$ alkylcarbonyl group or a $C_{6-18}$ arylcarbonyl group, and wherein the $C_{1-6}$ alkyl group, the $C_{1-6}$ alkylcarbonyl group and the $C_{6-18}$ arylcarbonyl group may be optionally substituted with a hydroxyl group.

3. The method of claim 1, wherein in the isolated compound of or its salt that is administered to the human, each of $R^1$ and $R^3$ is independently a hydrogen atom, $SO_3H$, a $C_{1-6}$ alkyl group, a $C_{1-6}$ alkylcarbonyl group or a $C_{6-18}$ arylcarbonyl group, wherein the $C_{1-6}$ alkyl group, the $C_{1-6}$ alkylcarbonyl group and the $C_{6-18}$ arylcarbonyl group may be optionally substituted with $NR^9R^{10}$, wherein each of $R^9$ and $R^{10}$ is independently a hydrogen atom or a $C_{1-6}$ alkyl group, or $R^9$ and $R^{10}$ mean, together with each other, $—(CH_2)_nX(CH_2)_m—$, wherein the $C_{1-6}$ alkyl group may be optionally substituted with a $C_{6-18}$ aryl group, wherein X is $CR^{11}R^{12}$, $NR^{13}$, O or S, wherein n is 1, 2 or 3, and m is 1, 2 or 3, provided that n+m is 3, 4 or 5, wherein each of $R^{11}$ and $R^{12}$ is independently a hydrogen atom or a $C_{1-6}$ alkyl group, wherein the $C_{1-6}$ alkyl group may be optionally substituted with a $C_{6-18}$ aryl group, wherein $R^{13}$ is a hydrogen atom or a $C_{1-6}$ alkyl group, and wherein the $C_{1-6}$ alkyl group may be optionally substituted with a $C_{6-18}$ aryl group.

4. The method of claim 1, wherein in the isolated compound of or its salt that is administered to the human, each of $R^1$ and $R^3$ is independently a hydrogen atom or a $C_{1-6}$ alkyl group.

5. The method of claim 4, wherein in the isolated compound or its salt that is administered to the human, each of $R^1$ and $R^3$ is independently a hydrogen atom or a methyl group, and each of $R^2$ and $R^4$ is independently a hydrogen atom, a hydroxyl group or a methoxy group.

6. The method of claim 1, claim 2, claim 3, claim 4 or claim 5, wherein in the isolated compound or its salt that is administered to the human, $R^2$ is a hydrogen atom.

7. The method of claim 6, wherein in the isolated compound or its salt that is administered to the human, each of $R^4$ and $R^a$ is independently a hydrogen atom or a methoxy group.

8. The method of claim 1, wherein the isolated compound or its salt that is administered to the human in need thereof is administered as a composition comprising the isolated compound of formula (1) or its salt and an excipient.

9. The method of claim 1, wherein the compound or its salt of formula (1) does not comprise a compound or its salt of formula (2):

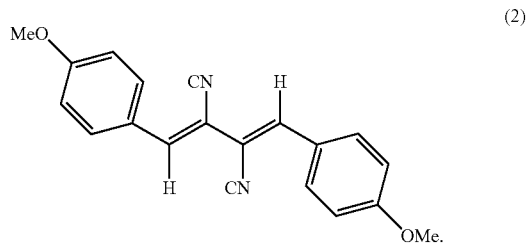

(2)

10. A method of increasing platelets in a human, the method comprising administering an isolated compound or its salt to the human in an amount sufficient to increase the platelets in the human, wherein the isolated compound or its salt is represented by the formula (1) or its salt,

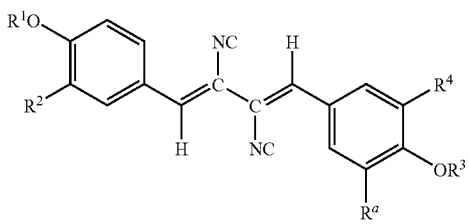

(1)

wherein each of $R^1$ and $R^3$ is independently a hydrogen atom, $SO_3H$, a $C_{1-6}$ alkyl group, a $C_{1-6}$ alkylcarbonyl group or a $C_{6-18}$ arylcarbonyl group, and wherein each of $R^2$, $R^4$ and $R^a$ is independently a hydrogen atom, a hydroxyl group or a $C_{1-6}$ alkoxy group;

wherein the $C_{1-6}$ alkyl group, the $C_{1-6}$ alkylcarbonyl group and the $C_{6-18}$ arylcarbonyl group may be optionally substituted with a halogen atom, a hydroxyl group, a $C_{2-6}$ alkenyl group, a $C_{1-6}$ alkoxy group, a $C_{1-6}$ alkoxycarbonyl group, a $C_{6-18}$ aryl group, a 2-pyridyl group, a 3-pyridyl group, a 4-pyridyl group, a 2-furanyl group, a 3-furanyl group, a 2-thienyl group, a 3-thienyl group or $NR^9R^{10}$, wherein the $C_{6-18}$ aryl group, the 2-pyridyl group, the 3-pyridyl group, the 4-pyridyl group, the 2-furanyl group, the 3-furanyl group, the 2-thienyl group and the 3-thienyl group may be optionally substituted with a halogen atom or a $C_{1-6}$ alkyl group, wherein each of $R^9$ and $R^{10}$ is independently a hydrogen atom or a $C_{1-6}$ alkyl group or $R^9$ and $R^{10}$ mean, together with each other, —$(CH_2)_nX(CH_2)_m$—, wherein the $C_{1-6}$ alkyl group may be optionally substituted with a $C_{6-18}$ aryl group wherein X is $CR^{11}R^{12}$, $NR^{13}$, O or S, wherein each of $R^{11}$ and $R^{12}$ is independently a hydrogen atom or a $C_{1-6}$ alkyl group, wherein $R^{13}$ is a hydrogen atom or a $C_{1-6}$ alkyl group that may be optionally substituted with a $C_{6-18}$ aryl group, wherein n is 1, 2 or 3, and m is 1, 2 or 3, provided that n+m is 3, 4 or 5, wherein the $C_{1-6}$ alkyl group may be optionally substituted with a $C_{6-18}$ aryl group, wherein $R^{13}$ is a hydrogen atom or a $C_{1-6}$ alkyl group, wherein the $C_{1-6}$ alkyl group may be optionally substituted with a $C_{6-18}$ aryl group, with the proviso that the compound of formula (1) or its salt does not comprise a compound of formula (2) or its salt

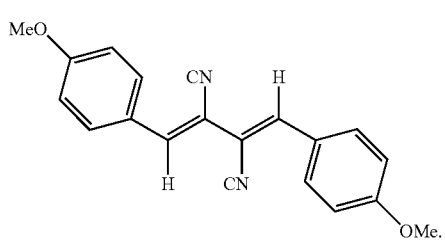

(2)

11. The method of claim 10, wherein in the isolated compound of or its salt that is administered to the human, each of $R^1$ and $R^3$ is independently a hydrogen atom, $SO_3H$, a $C_{1-6}$ alkyl group, a $C_{1-6}$ alkylcarbonyl group or a $C_{6-18}$ arylcarbonyl group, wherein the $C_{1-6}$ alkyl group, the $C_{1-6}$ alkylcarbonyl group and the $C_{6-18}$ arylcarbonyl group may be optionally substituted with a hydroxyl group, with the proviso that the compound of formula (1) or its salt does not comprise a compound of formula (2) or its salt

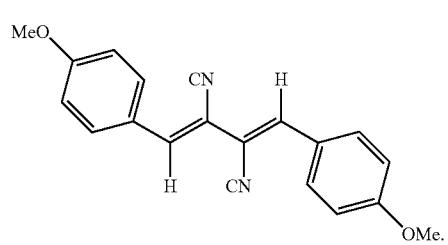

(2)

12. The method of claim 10, wherein in the isolated compound of or its salt that is administered to the human, each of $R^1$ and $R^3$ is independently a hydrogen atom, $SO_3H$, a $C_{1-6}$ alkyl group, a $C_{1-6}$ alkylcarbonyl group or a $C_{6-18}$ arylcarbonyl group, wherein the $C_{1-6}$ alkyl group, the $C_{1-6}$ alkylcarbonyl group and the $C_{6-18}$ arylcarbonyl group may be optionally substituted with $NR^9R^{10}$, wherein each of $R^9$ and $R^{10}$ is independently a hydrogen atom or a $C_{1-6}$ alkyl group, or $R^9$ and $R^{10}$ mean, together with each other, —$(CH_2)_nX(CH_2)_m$—, wherein the $C_{1-6}$ alkyl group may be optionally substituted with a $C_{6-18}$ aryl group, wherein X is $CR^{11}R^{12}$, $NR^{13}$, O or S, wherein n is 1, 2 or 3, and m is 1, 2 or 3, provided that n+m is 3, 4 or 5, wherein each of $R^{11}$ and $R^{12}$ is independently a hydrogen atom or a $C_{1-6}$ alkyl group, wherein the $C_{1-6}$ alkyl group may be optionally substituted with a $C_{6-18}$ aryl group, wherein $R^{13}$ is a hydrogen atom or a $C_{1-6}$ alkyl group,and wherein the $C_{1-6}$ alkyl group may be optionally substituted with a $C_{6-18}$ aryl group, with the proviso that the compound of formula (1) or its salt does not comprise a compound of formula (2) or its salt

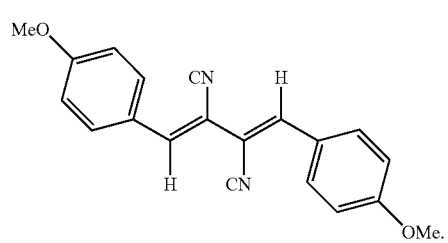

(2)

13. The method of claim 10, wherein in the isolated compound of or its salt that is administered to the human, each of $R^1$ and $R^3$ is independently a hydrogen atom or a $C_{1-6}$ alkyl group, with the proviso that the compound of formula (1) or its salt does not comprise a compound of formula (2) or its salt

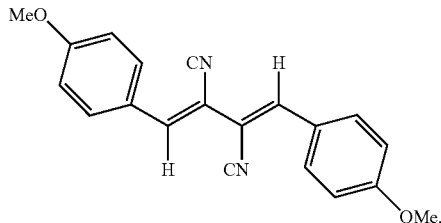
(2)

14. The method of claim 13, wherein in the isolated compound or its salt that is administered to the human,
each of $R^1$ and $R^3$ is independently a hydrogen atom or a methyl group, and
each of $R^2$ and $R^4$ is independently a hydrogen atom, a hydroxyl group or a methoxy group,
with the proviso that the compound of formula (1) or its salt does not comprise a compound of formula (2) or its salt

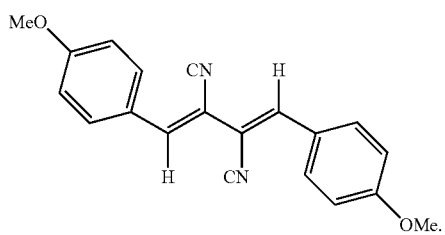
(2)

15. The method of claim 10, wherein in the isolated compound or its salt that is administered to the human, $R^2$ is a hydrogen atom, with the proviso that the compound of formula (1) or its salt does not comprise a compound of formula (2) or its salt

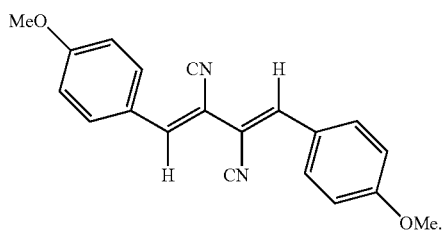
(2)

16. The method of claim 11, wherein in the isolated compound or its salt that is administered to the human, $R^2$ is a hydrogen atom, with the proviso that the compound of formula (1) or its salt does not comprise a compound of formula (2) or its salt

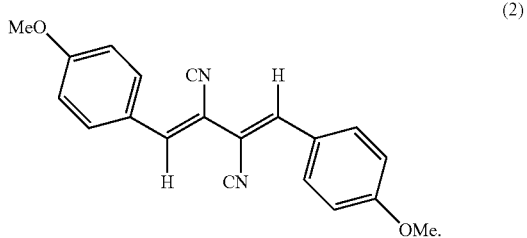
(2)

17. The method of claim 15, wherein in the isolated compound or its salt that is administered to the human, each of $R^4$ and $R^a$ is independently a hydrogen atom or a methoxy group, with the proviso that the compound of formula (1) or its salt does not comprise a compound of formula (2) or its salt

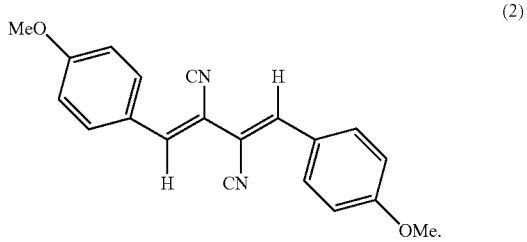
(2)

* * * * *

UNITED STATES PATENT AND TRADEMARK OFFICE
CERTIFICATE OF CORRECTION

| | | |
|---|---|---|
| PATENT NO. | : 7,851,503 B2 | |
| APPLICATION NO. | : 10/524666 | |
| DATED | : December 14, 2010 | |
| INVENTOR(S) | : Miyaji et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1098 days.

Signed and Sealed this
Fifth Day of July, 2011

David J. Kappos
*Director of the United States Patent and Trademark Office*